US012753167B2

United States Patent

(12) United States Patent
Chen et al.

(10) Patent No.: US 12,753,167 B2
(45) Date of Patent: Oct. 6, 2026

(54) INTERMEDIATE OF BILIVERDIN, AND PREPARATION METHOD AND USE THEREOF

(71) Applicant: WUHAN JIANMIN DAPENG PHARMACEUTICAL CO., LTD., Hubei (CN)

(72) Inventors: Fapu Chen, Wuhan (CN); Yuxin Shi, Wuhan (CN); Fakai Chen, Wuhan (CN)

(73) Assignee: WUHAN JIANMIN DAPENG PHARMACEUTICAL CO., LTD., Hubei (CN)

( * ) Notice: Subject to any disclaimer, the term of this patent is extended or adjusted under 35 U.S.C. 154(b) by 519 days.

(21) Appl. No.: 18/210,068

(22) Filed: Jun. 14, 2023

(65) Prior Publication Data

US 2023/0339914 A1 Oct. 26, 2023

Related U.S. Application Data

(63) Continuation-in-part of application No. PCT/CN2021/073782, filed on Jan. 26, 2021.

(30) Foreign Application Priority Data

Dec. 22, 2020 (CN) ......................... 202011527218.4

(51) Int. Cl.
*C07D 403/14* (2006.01)

(52) U.S. Cl.
CPC .................................. *C07D 403/14* (2013.01)

(58) Field of Classification Search
CPC .................................................... C07D 403/14
See application file for complete search history.

(56) References Cited

U.S. PATENT DOCUMENTS

2005/0209305 A1* 9/2005 Pendrak .................... A61P 9/00
435/118

* cited by examiner

*Primary Examiner* — Brian E McDowell
(74) *Attorney, Agent, or Firm* — JCIP GLOBAL INC.

(57) ABSTRACT

An intermediate of biliverdin represented by formula 1, and preparation method and use thereof:

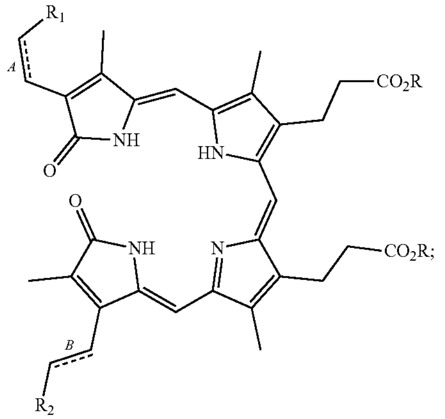

in formula 1, R is $C_1$-$C_5$ alkyl, or benzyl; "$\overline{---}$" at positions A and B independently represent a single bond or a double bond; when "$\overline{---}$" represents a single bond, $R_1$ or $R_2$ connected to the single bond is selected from one of tosyl, p-toluenesulfonyl, phenylsulfonyl, phenylsulfinyl; and when "$\overline{---}$" represents a double bond, $R_1$ or $R_2$ connected to the double bond is hydrogen.

8 Claims, No Drawings

INTERMEDIATE OF BILIVERDIN, AND PREPARATION METHOD AND USE THEREOF

CROSS-REFERENCE TO RELATED APPLICATIONS

This application is a continuation-in-part of International Patent Application No. PCT/CN2021/073782 with an international filing date of Jan. 26, 2021, designating the United States, now pending, and further claims foreign priority benefits to Chinese Patent Application No. 202011527218.4 filed Dec. 22, 2020. The contents of all of the aforementioned applications, including any intervening amendments thereto, are incorporated herein by reference.

BACKGROUND

The disclosure relates to the field of pharmaceutical synthesis, and more particularly to an intermediate of biliverdin, and preparation method and use thereof.

Biliverdin is a tetrapyrrole compound obtained from the hydrolysis of heme by hemeoxygenase-1 (HO-1). Biliverdin is an intermediate of metabolism and circulation system of heme, and can initiate physiological functions such as anti-inflammatory and immune regulation, to improve liver function, reduce alanine transaminase, alleviate ischemia reperfusion injury caused by liver transplantation, inhibit vascular remodeling caused by the formation of new tunica intima, and inhibit bovine diarrhea virus replication.

In addition, bilirubin is a main raw material for in vitro cultivation of bezoar. Biliverdin can be used to prepare bilirubin, and biliverdin is also an important pharmaceutical intermediate.

Typically, the preparation of biliverdin includes extraction, chemical conversion, enzymatic conversion and biosynthesis. Due to the limited source of raw materials and the easy formation of multiple isomers during the extraction process of bilirubin, the yield and purity of the product bilirubin are low. It was previously reported that chemical oxidation of heme was used to prepare biliverdin, which produced more isomers with lower yield than other methods. At present, there are reports on the conversion of biliverdin from heme by enzymatic conversion and biosynthesis, but the selectivity of oxidative ring opening is not high, and the source of heme is limited, the price is high, so it is not suitable for industrial production.

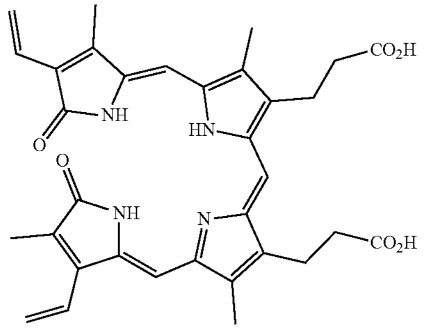

biliverdin

A conventional synthetic method of biliverdin uses benzyl chloroethyl pyrrole formate as raw material. After a series of reactions, dipyrrole methane is obtained and condensed to generate pyrroline, which is hydrolyzed to generate 3,18-dichloroethyl biliverdin dimethyl ester. The method involves many reaction steps, has low yield, high cost, and some steps are highly polluting. Many intermediate products need to be separated by chromatography, so the method is not suitable for industrial production.

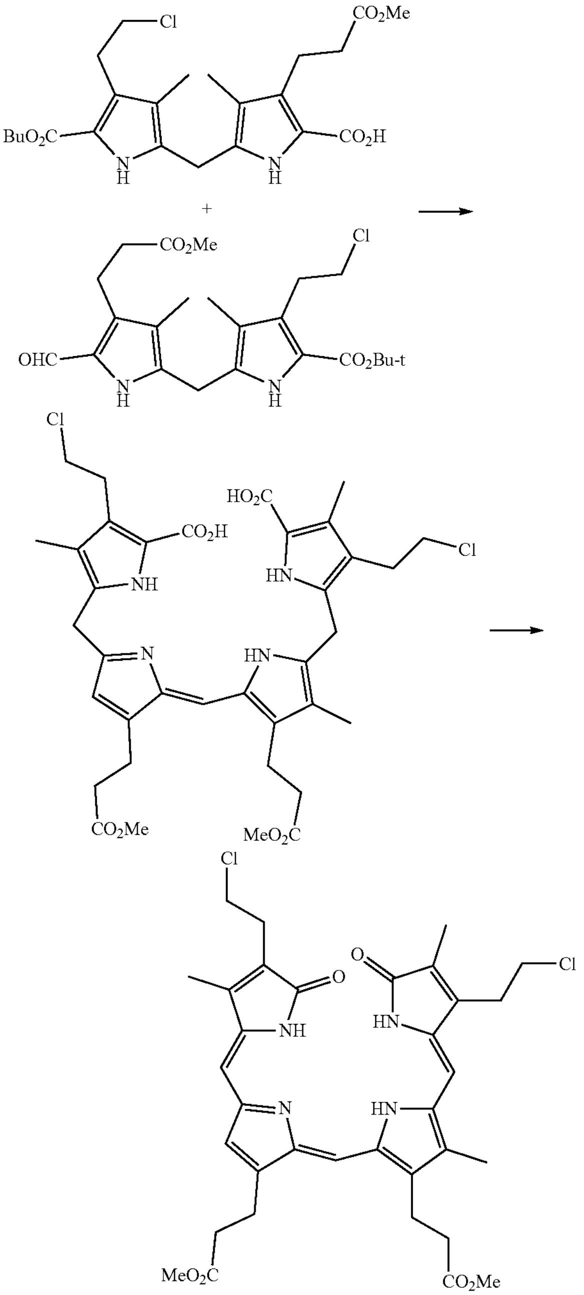

SUMMARY

In view of the problems in the conventional synthesis of biliverdin, such as low yield, high by-products, high cost, difficult extraction, etc., the disclosure provides a new intermediate of biliverdin.

In one aspect, the disclosure provides an intermediate of biliverdin represented by formula 1:

1

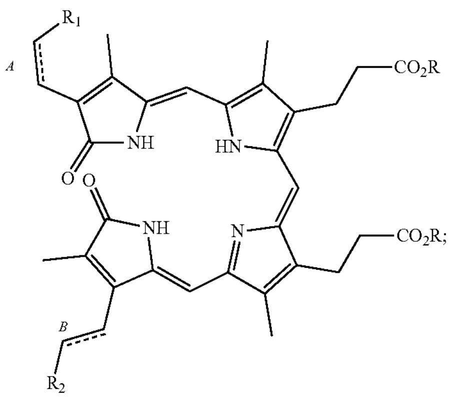

where, R is hydrogen, $C_1$-$C_5$ alkyl, or benzyl; "⎓" at positions A and B independently represent a single bond or a double bond; when "⎓" represents a single bond, $R_1$ or $R_2$ connected to the single bond is selected from p-toluenesulfonyl, p-toluenesulfinyl, phenylsulfonyl, and phenylsulfinyl; and when "⎓" represents a double bond, $R_1$ or $R_2$ connected to the double bond is hydrogen.

In a class of this embodiment, R is hydrogen or $C_1$-$C_5$ alkyl; "⎓" at positions A and B independently represent a single bond or a double bond; when "⎓" represents a single bond, $R_1$ or $R_2$ connected to the single bond is selected from p-toluenesulfonyl and p-toluenesulfinyl; and when "⎓" represents a double bond, $R_1$ or $R_2$ connected to the double bond is hydrogen.

In a class of this embodiment, the intermediate of biliverdin represented by formula 1 is one of the following compounds:

2

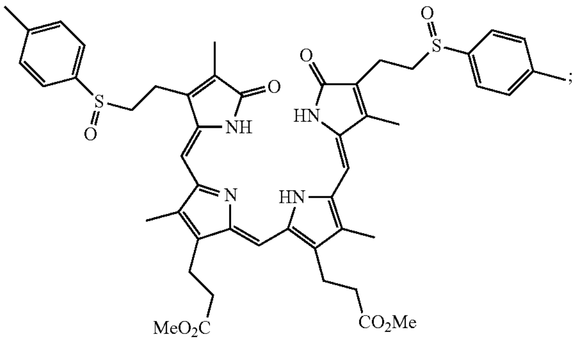

-continued

3

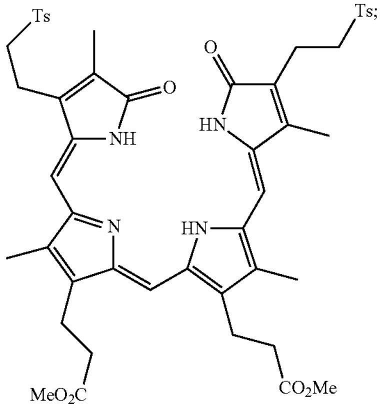

4

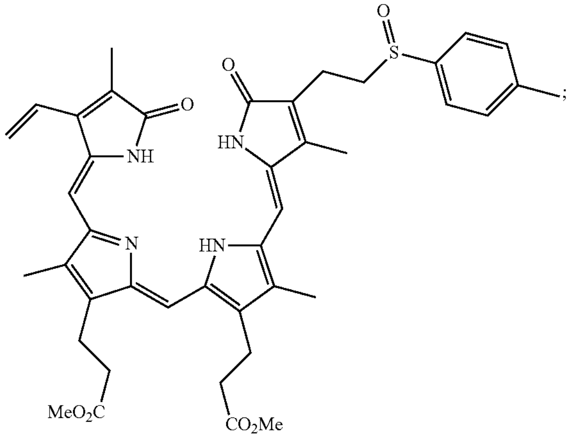

5

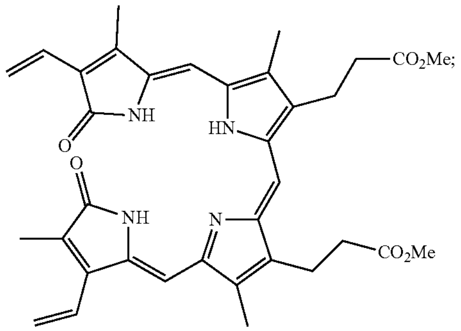

6

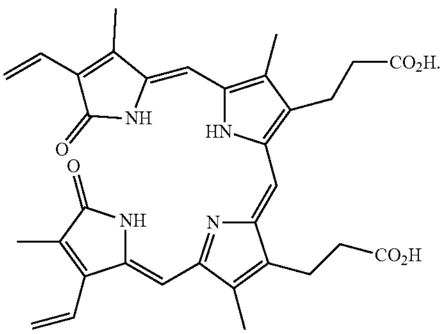

In a second aspect, the disclosure provides a method for preparing the intermediate of biliverdin, the method comprising contacting a compound represented by formula 7 and a compound represented by formula 8 for a condensation reaction:

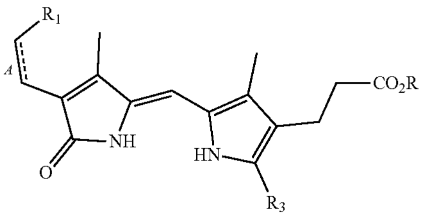

7

+

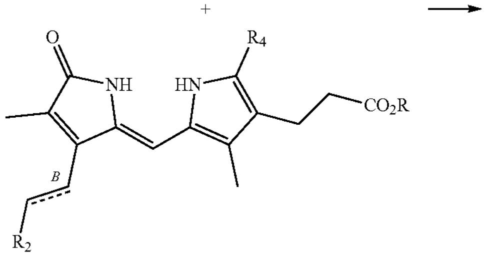

8

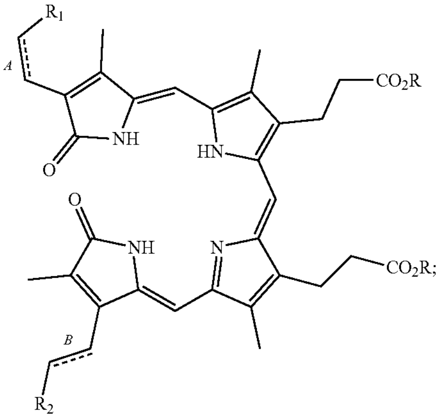

1 where, R is hydrogen, $C_1$-$C_5$ alkyl, or benzyl; “=== ” at positions A and B independently represent a single bond or a double bond; when “=== ” represents a single bond, $R_1$ or $R_2$ connected to the single bond is selected from p-toluenesulfonyl, p-toluenesulfinyl, phenylsulfonyl, phenylsulfinyl; when “=== ” represents a double bond, $R_1$ or $R_2$ connected to the double bond is hydrogen; and one of $R_3$ and $R_4$ is a formyl, and the other is tert-butoxycarbonyl or hydrogen.

In a class of this embodiment, the condensation reaction is carried out in the presence of an acid as a catalyst.

In a class of this embodiment, the acid is hydrochloric acid, sulfuric acid, trifluoroacetic acid, formic acid, acetic acid, benzenesulfonic acid, p-toluenesulfonic acid, or a mixture thereof preferably, hydrochloric acid, sulfuric acid, trifluoroacetic acid, or a mixture thereof.

In a class of this embodiment, the condensation reaction involves a solvent selected from $C_1$-$C_6$ alcohol, dichloromethane, tetrahydrofuran, 1,2-dichloroethane, ethyl acetate, acetone, or a mixture thereof; preferably, methanol, ethanol, isopropanol, or a mixture thereof.

In a class of this embodiment, the condensation reaction is carried out at a temperature of between 20° C. and 35° C.

In a class of this embodiment, a molar ratio of the compound 7 to the compound 8 to the acid is 1:(0.5-2):(0.1-0.5), preferably, 1:(0.8-1.2):(0.1-0.3).

In a third aspect, the disclosure provides use of the intermediate of biliverdin for preparation of biliverdin or a derivative thereof. Specifically, the use of the compound 3, 4 or 5 in preparation of biliverdin dimethyl ester.

In a fourth aspect, the disclosure provides a method for preparation of biliverdin or a derivative thereof; in formula 1, when “=== ” at positions A and B both represent a double bond, R is hydrogen, $C_1$-$C_5$ alkyl, or benzyl; the compound represented by formula 1 is biliverdin or a derivative thereof, which can be prepared by the compound represented by formula 7 and the compound represented by formula 8 through a condensation reaction:

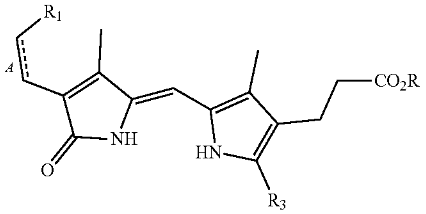

7

+

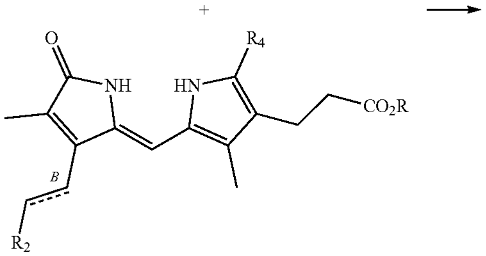

8

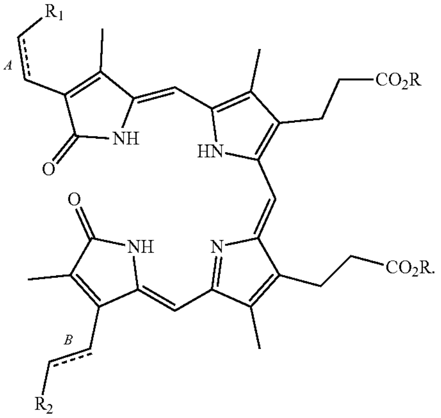

1

R is hydrogen, $C_1$-$C_5$ alkyl, or benzyl; “=== ” at positions A and B both represent a double bond, and both $R_1$ and $R_2$ are hydrogen; one of $R_3$ and $R_4$ is a formyl, and the other is tert-butoxycarbonyl or hydrogen. Preferably, R is hydrogen or methyl.

In a class of this embodiment, the condensation reaction is carried out in the presence of an acid as a catalyst.

In a class of this embodiment, the acid is hydrochloric acid, sulfuric acid, trifluoroacetic acid, formic acid, acetic acid, benzenesulfonic acid, p-toluenesulfonic acid, or a mixture thereof.

In a class of this embodiment, the condensation reaction involves a solvent selected from $C_1$-$C_6$ alcohol, dichloromethane, tetrahydrofuran, 1,2-dichloroethane, ethyl acetate, acetone, or a mixture thereof.

In a class of this embodiment, the condensation reaction is carried out at a temperature of between −10° C. and 35° C.

In a class of this embodiment, the molar ratio of the compound 7 to the compound 8 to the acid is 1:(0.5-2):(0.1-0.5).

In a fifth aspect, the disclosure provides a method for preparing biliverdin or a derivative thereof, the method comprising heating the compound represented by formula 1.

In a class of this embodiment, the method comprises heating the compound represented by formula 1, particularly, by formula 2, 3 or 4.

In a class of this embodiment, a solvent used for the heating reaction is selected from one or more of a substituted benzene, pyrrolidone, DMF, and THF. When the heating reaction is carried out in the aforementioned solvent, the reaction yield can reach 45% or more.

In a class of this embodiment, the solvent is xylene, nitrobenzene, chlorobenzene, DMF, THF, or a mixture thereof.

In a class of this embodiment, the temperature for heating reaction is 100-160° C. When the reaction temperature is controlled at 100-160° C., the reaction yield reaches over 45%.

In a class of this embodiment, the temperature for heating reaction is 130-150° C. When the reaction temperature is controlled at 130-150° C. in the presence of the solvent, the reaction yield reaches 60% or more.

In a class of this embodiment, the biliverdin or a derivative thereof is prepared in the presence of a catalyst.

In a class of this embodiment, the catalyst is an organic base. When the organic base is added as a catalyst in the reaction system and the reaction temperature is controlled between 130 and 150° C., the reaction yield can reach 70% or more in the presence of an appropriate solvent.

In a class of this embodiment, the organic base is pyridine, sodium ethoxide, or a mixture thereof, and the reaction yield can reach no less than 73%.

In a class of this embodiment, the produced biliverdin or a derivative thereof is biliverdin or biliverdin dimethyl ester.

The following advantages are associated with the intermediate of biliverdin, and preparation method and use thereof of the disclosure:

1. The intermediate of biliverdin or its analogues of the disclosure can be used to prepare biliverdin or its analogues. The preparation method is simple, efficient, cost-effective, and easy to industrialization.

2. The preparation method of the intermediate of biliverdin or its analogues of the disclosure is easy to practice; the conditions are mild, and the method can be carried out at room temperature with low cost.

3. The preparation method of the intermediate of biliverdin or its analogues is easy to practice and industrialize.

DETAILED DESCRIPTION

To further illustrate the disclosure, embodiments detailing an intermediate of biliverdin, and preparation method and use thereof are described below. It should be noted that the following embodiments are intended to describe and not to limit the disclosure.

The disclosure provides an intermediate of biliverdin, and preparation method and use thereof, also provides biliverdin, and preparation method and use thereof.

Intermediate of Biliverdin

The intermediate of biliverdin is represented by formula 1:

1

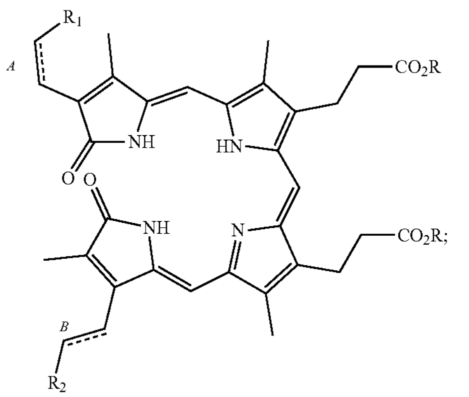

where, R is hydrogen, $C_1$-$C_5$ alkyl, or benzyl; "⎓ " at positions A and B independently represent a single bond or a double bond; when "⎓ " represents a single bond, $R_1$ or $R_2$ connected to the single bond is selected from p-toluenesulfonyl, p-toluenesulfinyl, phenylsulfonyl, and phenylsulfinyl; and when "⎓ " represents a double bond, $R_1$ or $R_2$ connected to the double bond is hydrogen.

Preferably, the intermediate of biliverdin or a derivative thereof has a formula 1 as follows:

2

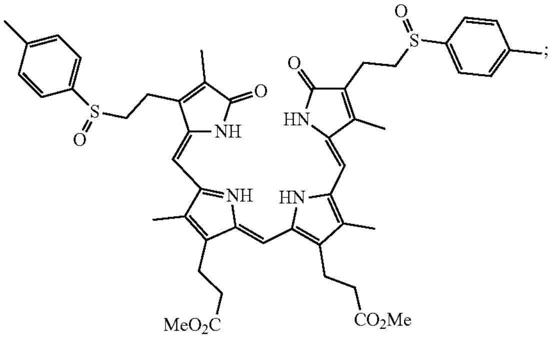

3

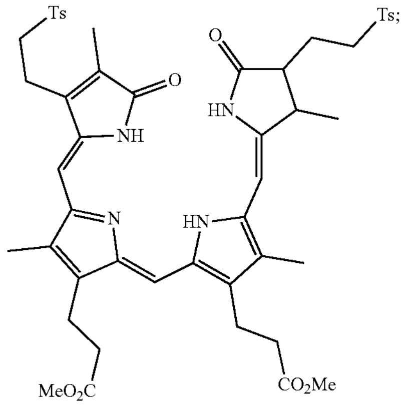

-continued

4

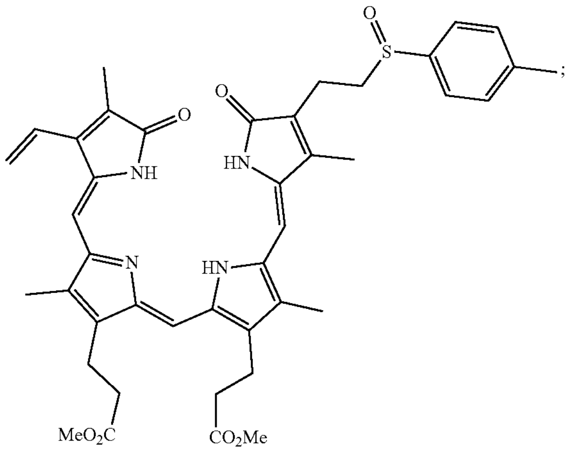

5

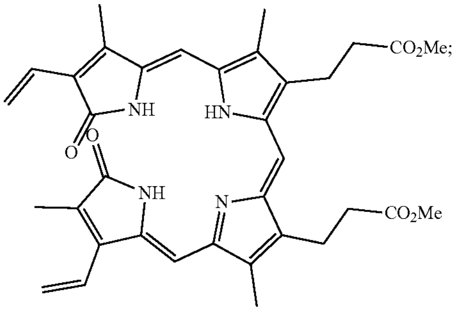

6

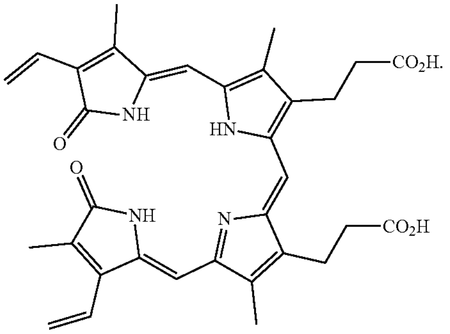

Method for Preparing the Intermediate of Biliverdin

The disclosure provides a method for preparing the intermediate of biliverdin, the method comprising contacting a compound represented by formula 7 and a compound represented by formula 8 for a condensation reaction:

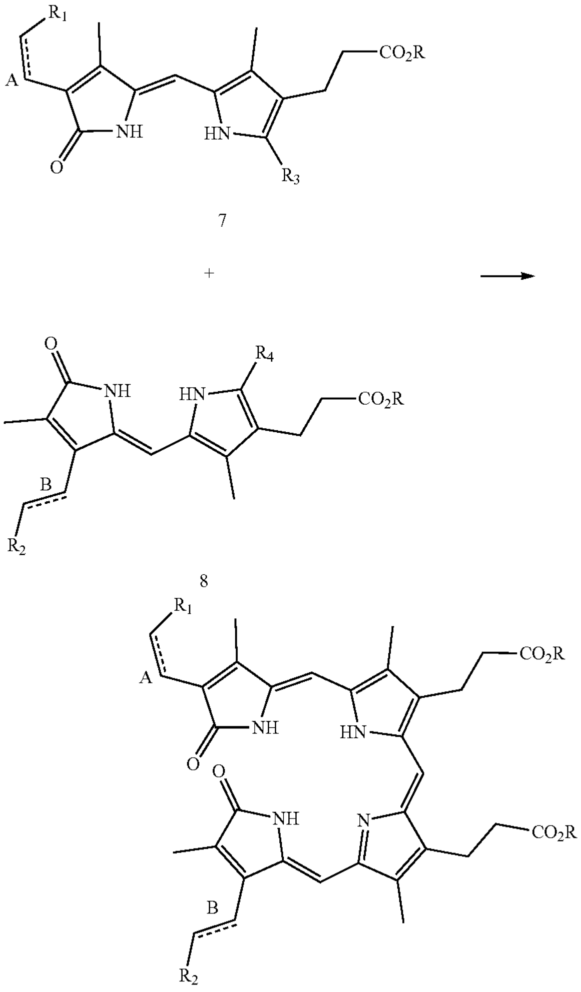

7

8

1 where, R is hydrogen, $C_1$-$C_5$ alkyl, or benzyl; "$\overline{---}$ " at positions A and B independently represent a single bond or a double bond; when "$\overline{---}$ " represents a single bond, $R_1$ or $R_2$ connected to the single bond is selected from p-toluenesulfonyl, p-toluenesulfinyl, phenylsulfonyl, phenylsulfinyl; when "$\overline{---}$ " represents a double bond, $R_1$ or $R_2$ connected to the double bond is hydrogen; and one of $R_3$ and $R_4$ is a formyl, and the other is tert-butoxycarbonyl or hydrogen.

In a class of this embodiment, the condensation reaction is carried out in the presence of an acid as a catalyst.

In a class of this embodiment, the acid is hydrochloric acid, sulfuric acid, trifluoroacetic acid, formic acid, acetic acid, benzenesulfonic acid, p-toluenesulfonic acid, or a mixture thereof; preferably, hydrochloric acid, sulfuric acid, trifluoroacetic acid, or a mixture thereof.

In a class of this embodiment, the condensation reaction involves a solvent selected from $C_1$-$C_6$ alcohol, dichloromethane, tetrahydrofuran, 1,2-dichloroethane, ethyl acetate, acetone, or a mixture thereof; preferably, methanol, ethanol, isopropanol, or a mixture thereof.

In a class of this embodiment, the condensation reaction is carried out at a temperature of between 20° C. and 35° C.

In a class of this embodiment, a molar ratio of the compound 7 to the compound 8 to the acid is 1:(0.5-2):(0.1-0.5), preferably, 1:(0.8-1.2):(0.1-0.3).

Use of the Intermediate of Biliverdin

The disclosure provides use of the intermediate of biliverdin for preparation of biliverdin or a derivative thereof. Specifically, the use of the compound 3, 4 or 5 in preparation of biliverdin dimethyl ester.

Method for Preparation of Biliverdin or a Derivative Thereof

In formula 1, when "===" at positions A and B both represent a double bond, R is hydrogen, $C_1$-$C_5$ alkyl, or benzyl; the compound represented by formula 1 is biliverdin or a derivative thereof, which can be prepared by the compound represented by formula 7 and the compound represented by formula 8 through a condensation reaction:

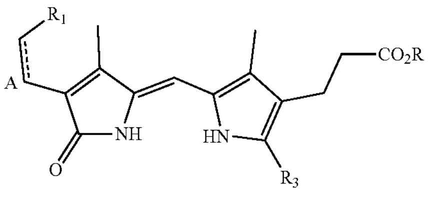

7

+

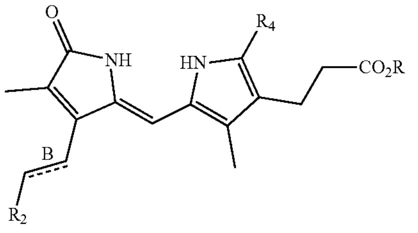

8

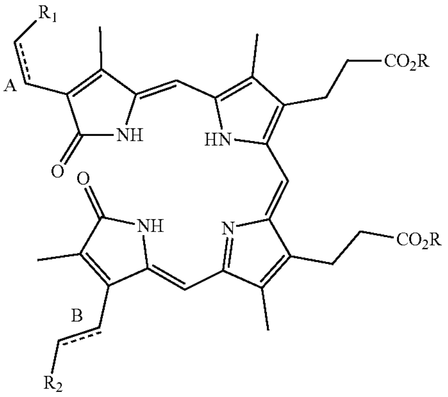

1

R is hydrogen, $C_1$-$C_5$ alkyl, or benzyl; "===" at positions A and B both represent a double bond, and both $R_1$ and $R_2$ are hydrogen; one of $R_3$ and $R_4$ is a formyl, and the other is tert-butoxycarbonyl or hydrogen. Preferably, R is hydrogen or methyl.

In a class of this embodiment, the condensation reaction is carried out in the presence of an acid as a catalyst.

In a class of this embodiment, the acid is hydrochloric acid, sulfuric acid, trifluoroacetic acid, formic acid, acetic acid, benzenesulfonic acid, p-toluenesulfonic acid, or a mixture thereof.

In a class of this embodiment, the condensation reaction involves a solvent selected from $C_1$-$C_6$ alcohol, dichloromethane, tetrahydrofuran, 1,2-dichloroethane, ethyl acetate, acetone, or a mixture thereof.

In a class of this embodiment, the condensation reaction is carried out at a temperature of between −10° C. and 35° C.

In a class of this embodiment, the molar ratio of the compound 7 to the compound 8 to the acid is 1:(0.5-2):(0.1-0.5). Optionally, biliverdin or its analogue of the disclosure is biliverdin or biliverdin dimethyl ester Method for Preparing Biliverdin or a Derivative Thereof The disclosure provides a method for preparing biliverdin or a derivative thereof.

The method comprises heating the compound represented by formula 1, particularly, by formula 2, 3 or 4.

In a class of this embodiment, a solvent used for the heating reaction is selected from one or more of a substituted benzene, pyrrolidone, DMF, and THF. When the heating reaction is carried out in the aforementioned solvent, the reaction yield can reach 45% or more.

In a class of this embodiment, the solvent is xylene, nitrobenzene, chlorobenzene, DMF, THF, or a mixture thereof.

In a class of this embodiment, the temperature for heating reaction is 100-160° C. When the reaction temperature is controlled at 100-160° C., the reaction yield reaches over 45%.

In a class of this embodiment, the temperature for heating reaction is 130-150° C. When the reaction temperature is controlled at 130-150° C. in the presence of the solvent, the reaction yield reaches 60% or more.

In a class of this embodiment, the biliverdin or a derivative thereof is prepared in the presence of a catalyst.

In a class of this embodiment, the catalyst is an organic base. When the organic base is added as a catalyst in the reaction system and the reaction temperature is controlled between 130 and 150° C., the reaction yield can reach 70% or more in the presence of an appropriate solvent.

In a class of this embodiment, the organic base is pyridine, sodium ethoxide, or a mixture thereof, and the reaction yield can reach no less than 73%.

In a class of this embodiment, the produced biliverdin or a derivative thereof is biliverdin or biliverdin dimethyl ester.

If no specific technology or conditions are stated in the disclosure, the technology or conditions described in the related art or the product manual should be followed. Nuclear magnetic resonance (NMR) was measured using Bruker-AMX400 nuclear magnetic resonance instrument. ESI-MS was measured using Finnigan-MAT-95 mass spectrometer. All reagents are analytical pure (Sinopharm Chemical Reagent Co., Ltd.). In the following examples, 1,5-Dihydro-4-methyl-3-(2-p-toluenesulfoethyl)-5-nenen-eba p-toluenesulfonyl-2H-2-pyrrolidone (shown in Formula 21) Refer to the reference Chem Lett., 2001, prepared using methods 6590-591; 9-tert-butyloxycarbonyl-3,7-dimethyl-8-(2-methoxycarbonyl ethyl)-2-(2-neneneba p-toluenesulfonyl ethyl)-dipyrrolomethen-1-one (shown in Formula 12), 9-formyl-2,7-dimethyl-8-(2-methoxycarbonyl ethyl)-3-vinyldipyrrolomethen-1-one (shown in Formula 15) Refer to the literature Angelw Chem. Int. Ed., 1998, 37, 13-14, 1843-1846 method preparation; 3,7-Dimethyl-8-(2-methoxycarbonylethyl)-2-vinyl-dipyrrolidene-1-one (shown in formula 17), according to reference Org. Lett, 2001, 3, 827-830 method preparation; 9-tert-butyloxycarbonyl-3,7-dimethyl-8-(2-methoxycarbonyl ethyl)-2-vinyl-dipyrrolomethen-1-one (shown in Formula 16), 5-formyl-3-methoxycarbonyl ethyl-tert-butyl 4-methylpyrrolic acid (shown in Formula 22), 9-formyl-2,7-dimethyl-8-(2-methoxycarbonyl ethyl)-3-(2-p-tolylene sulfonyl group ethyl)-dipyrrolomethen-1-one (shown in Formula 30) Refer to reference Bull Chem. Soc. Jpn., 1994, 67, 3088-3093 method preparation; 9-tert-butyloxycarbonyl-3,7-dimethyl-8-(2-methoxycarbonyl ethyl)-2-(2-neneneba p-toluenesulfonyl ethyl)-dipyrrolomethen-1-one (shown in Formula 18), 9-formyl-2,7-dimethyl-8-(2-methoxycarbonyl ethyl)-3-(2-p-toluenesulfonyl ethyl)-dipyrrolomethen-1-one (shown in Formula 23), refer to the reference Bull Chem. Soc. Jpn., 1994, 67, 3088-3093 method preparation; 2,2-dimethoxypropylamine (shown in formula 28) according to literature Euro J. Med. Chem., 1995, 30, 931-942 method preparation; 4-p-Toluenesulfobutyryl chloride (shown in formula 29) was prepared according to the method described in literature MedChemComm, 2017, 8, 1268-1274.

Example 1

Synthesis of 3,3'-(3,18-di (2-p-tolylene sulfonyl group ethyl)-2,7,13,17-tetramethyl-1,19-dioxo-1,19,22,24-tetrahydro-21H-8,12-porphyrinyl)-dimethyl Dipropionate (Shown in Formula 2)

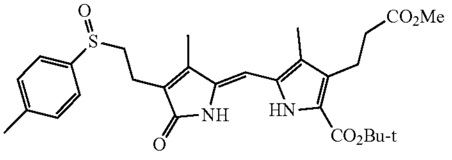

9

+

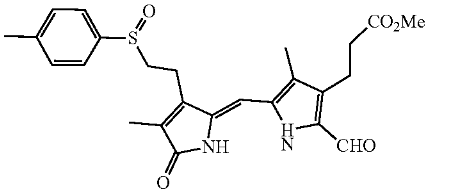

10

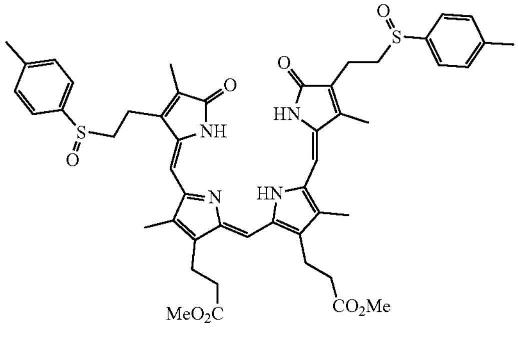

2

1.00 g of 9-tert-butyloxycarbonyl-3,7-dimethyl-8-(2-methoxycarbonyl ethyl)-2-(2-p-tolylene sulfonyl group ethyl)-dipyrrolomethen-1-one (shown in formula 9) was dissolved in 5 mL of trifluoroacetic acid and stirred at 25° C. for 30 minutes. 0.87 g of 9-formyl-2,7-dimethyl-8-(2-methoxycarbonyl ethyl)-3-(2-p-tolylene sulfonyl group ethyl)-dipyrrolomethen-1-one (shown in formula 10) was added to the resulting mixture and stirred at 25° C. for 10 hours, and then 20 mL of dichloromethane was added. The organic layer was collected, washed with saturated sodium bicarbonate to neutral, dried over anhydrous sodium sulfate, filtered, and recrystallized with ethanol to yield 0.85 g of blue-green solid, i.e. 3,3'-(3,18-di (2-p-tolylene sulfonyl group ethyl)-2,7,13,17-tetramethyl-1,19-dioxo-1,19,22,24-tetrahydro-21H-8,12-porphyrinyl)-dimethyl dipropionate (shown in Formula 2), with a yield of 51%. $^1$H NMR (400 MHz, $CDCl_3$): δ 1.52 (s, 3H), 1.93 (s, 3H), 1.95 (s, 3H), 1.99 (s, 3H), 2.34 (s, 3H), 2.40 (s, 3H), 2.51-2.65 (m, 6H), 2.87 (t, J=7.2 Hz, 2H), 2.96 (t, J=7.2 Hz, 2H), 3.27 (t, J=7.2 Hz, 2H), 3.66 (s, 3H), 3.67 (s, 3H), 5.55 (s, 1H), 5.75 (s, 1H), 6.66 (s, 1H), 7.14 (d, J=8.0 Hz, 2H), 7.30 (d, J=8.0 Hz, 2H), 7.33 (d, J=8.0 Hz, 2H), 7.76 (d, J=8.0 Hz, 2H); ESI-Mass: 891.34 $(M+1)^+$.

Example 2

Synthesis of 3,3'-(3,18-di (2-p-tolylene sulfonyl group ethyl)-2,7,13,17-tetramethyl-1,19-dioxo-1,19,22,24-tetrahydro-21H-8,12-porphyrinyl)-dimethyl Dipropionate (Shown in Formula 2)

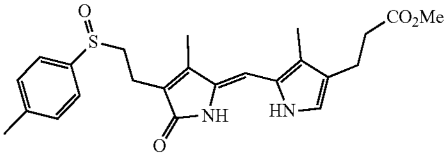

11

+

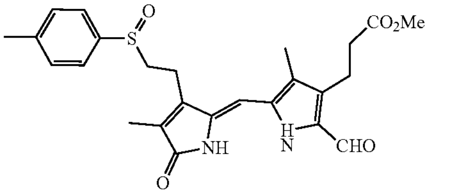

10

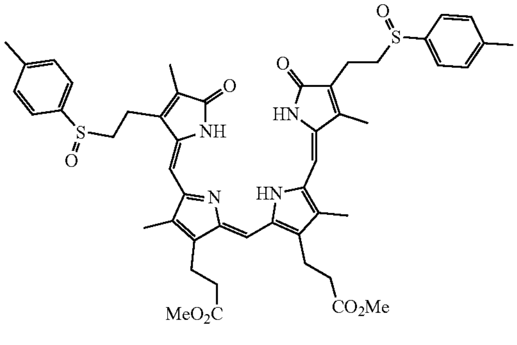

2

1.00 g of 3,7-dimethyl-8-(2-methoxycarbonyl ethyl)-2-(2-p-tolylene sulfonyl group ethyl)-dipyrrolomethen-1-one (shown in Formula 11) and 0.87 g of 9-formyl-2,7-dimethyl-8-(2-methoxycarbonyl ethyl)-3-(2-p-tolylene sulfonyl group ethyl)-dipyrrolomethen-1-one (shown in Formula 10) were mixed and dissolved in 50 mL of methanol, and then 1.5 mL of 1M hydrogen chloride methanol solution was added. The resulting mixture was stirred at 15° C. for 10 hours, concentrated under reduced pressure, dissolved in dichloromethane, and washed with saturated sodium bicarbonate to neutral. The organic layer was collected, dried over anhydrous sodium sulfate, filtered, and recrystallized with ethanol to yield 1.09 g of blue-green solid, that is, 3,3'-(3,18-di (2-p-tolylene sulfonyl group ethyl)-2,7,13,17-tetramethyl-1,19-dioxo-1,19,22,24-tetrahydro-21H-8,12-porphyrin)-dimethyl dipropionate (shown in Formula 2), with a yield of 66%.

Example 3

Synthesis of 3,3'-(3,18-di (2-p-tolylene sulfonyl group ethyl)-2,7,13,17-tetramethyl-1,19-dioxo-1,19,22,24-tetrahydro-21H-8,12-porphyrinyl)-dimethyl Dipropionate (Shown in Formula 2)

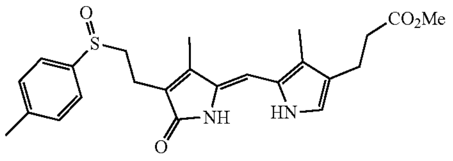

式 11

+

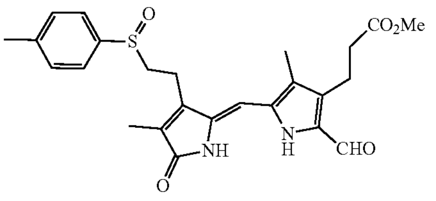

式 10

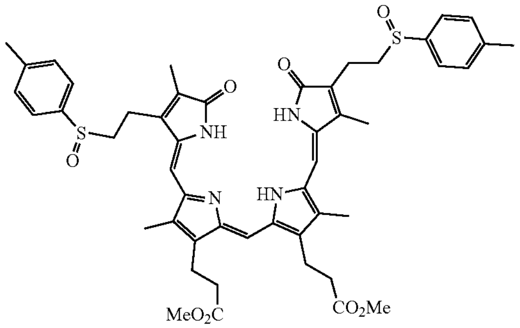

式 2

1.00 g of 3,7-dimethyl-8-(2-methoxycarbonyl ethyl)-2-(2-p-tolylene sulfonyl group ethyl)-dipyrrolomethen-1-one (shown in Formula 11) and 0.87 g of 9-formyl-2,7-dimethyl-8-(2-methoxycarbonyl ethyl)-3-(2-p-tolylene sulfonyl group ethyl)-dipyrrolomethen-1-one (shown in Formula 10) were mixed and dissolved in 50 mL of ethanol, and then 0.5 mL of concentrated sulfuric acid was added. The resulting mixture was stirred at 35° C. for 10 hours, concentrated under reduced pressure, dissolved in dichloromethane, and washed with saturated sodium bicarbonate to neutral. The organic layer was collected, dried over anhydrous sodium sulfate, filtered, and recrystallized with ethanol to yield 1.19 g of blue-green solid, that is, 3,3'-(3,18-di (2-p-tolylene sulfonyl group ethyl)-2,7,13,17-tetramethyl-1,19-dioxo-1,19,22,24-tetrahydro-21H-8,12-porphyrin)-dimethyl dipropionate (shown in Formula 2), with a yield of 72%.

Example 4

Synthesis of 3,3'-(3,18-bis (2-neneneba p-toluenesulfonyl ethyl)-2,7,13,17-tetramethyl-1,19-dioxo-1,19,22,24-tetrahydro-21H-8,12-porphyrin)-dipropionate Dimethyl Ester (Shown in Formula 3)

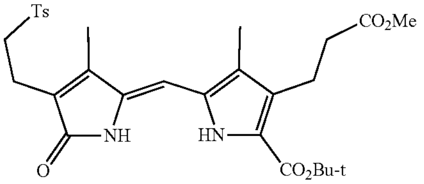

+

12

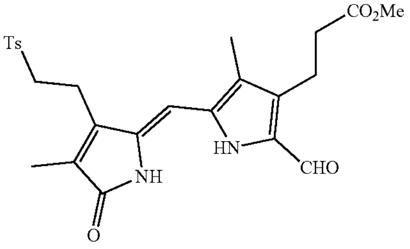

13

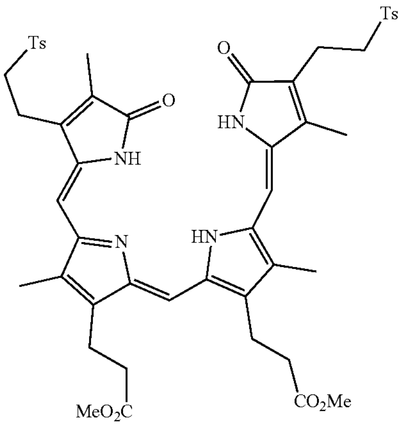

3

Ts: 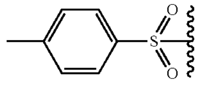

1.00 g of 9-tert-butyloxycarbonyl-3,7-dimethyl-8-(2-methoxycarbonyl ethyl)-2-(2-neneneba p-toluenesulfonyl ethyl)-dipyrrolomethen-1-one (shown in formula 12) was dissolved in 5 mL of trifluoroacetic acid and stirred at 25° C. for 30 minutes. 0.87 g of 9-formyl-2,7-dimethyl-8-(2-methoxycarbonyl ethyl)-3-(2-neneneba p-toluenesulfonyl ethyl)-dipyrrolomethen-1-one (shown in formula 13) was added to the resulting mixture and stirred at 25° C. for 10 hours. The mixture was concentrated under reduced pressure, dissolved in dichloromethane, and washed with saturated sodium bicarbonate to neutral. The organic layer was collected, dried over anhydrous sodium sulfate, filtered, and recrystallized with ethanol to yield 0.91 g of a blue-green solid, i.e. 3,3'-(3,18-bis (2-neneneba p-toluenesulfonyl ethyl)-2,7,13,17-tetramethyl-1,19-dioxo-1,19,22,24-tetrahydro-21H-8,12-porphyrin)-dipropionate dimethyl ester (shown in Formula 3), with a yield of 55%. $^1$H NMR (400 MHz, $CDCl_3$): δ 1.52 (s, 3H), 1.93 (s, 3H), 1.95 (s, 3H), 1.99 (s, 3H), 2.34 (s, 3H), 2.40 (s, 3H), 2.51-2.65 (m, 6H), 2.87 (t, J=7.2 Hz, 2H), 2.96 (t, J=7.2 Hz, 2H), 3.27 (t, J=7.2 Hz, 2H), 3.66 (s, 3H), 3.67 (s, 3H), 5.55 (s, 1H), 5.75 (s, 1H), 6.66 (s, 1H), 7.14 (d, J=8.0 Hz, 2H), 7.30 (d, J=8.0 Hz, 2H), 7.33 (d, J=8.0 Hz, 2H), 7.76 (d, J=8.0 Hz, 2H); ESI-Mass: 945.34 $(M+Na)^+$.

Example 5

Synthesis of 3,3'-(3,18-bis (2-neneneba p-toluenesulfonyl ethyl)-2,7,13,17-tetramethyl-1,19-dioxo-1,19,22,24-tetrahydro-21H-8,12-porphyrin)-dipropionate Dimethyl Ester (Shown in Formula 3)

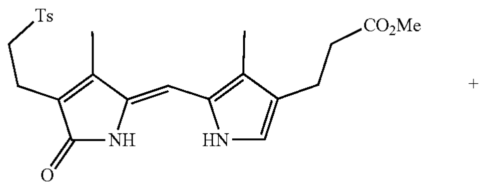

14

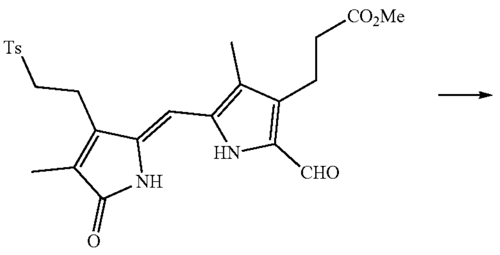

13

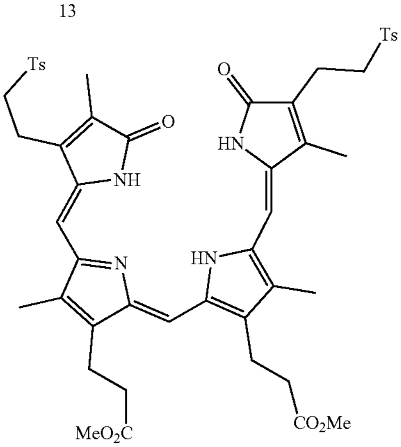

3

1.00 g of 3,7-dimethyl-8-(2-methoxycarbonyl ethyl)-2-(2-neneneba p-toluenesulfonyl ethyl)-dipyrrolomethen-1-one (shown in Formula 14) and 0.87 g of 9-formyl-2,7-dimethyl-8-(2-methoxycarbonyl ethyl)-3-(2-neneneba p-toluenesulfonyl ethyl)-dipyrrolomethen-1-one (shown in Formula 13) were mixed and dissolved in 50 mL of isopropanol, and then 0.5 mL of concentrated sulfuric acid was added. The resulting mixture was stirred at 30° C. for 10 hours, concentrated under reduced pressure, dissolved in dichloromethane, and washed with saturated sodium bicarbonate to neutral. The organic layer was collected, dried over anhydrous sodium sulfate, filtered, and recrystallized with ethanol to yield 1.04 g of blue-green solid, that is, 3,3'-(3,18-bis (2-neneneba p-toluenesulfonyl ethyl)-2,7,13,17-tetramethyl-1,19-dioxo-1,19,22,24-tetrahydro-21H-8,12-porphyrin)-dipropionate dimethyl ester (shown in Formula 3), with a yield of 63%.

Example 6

Synthesis of 3,3'-(3,18-bis (2-neneneba p-toluenesulfonyl ethyl)-2,7,13,17-tetramethyl-1,19-dioxo-1,19,22,24-tetrahydro-21H-8,12-porphyrin)-dipropionate Dimethyl Ester (shown in Formula 3)

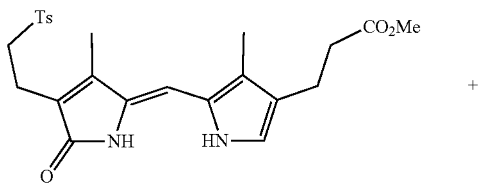

14

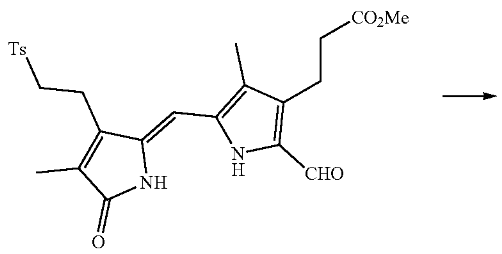

13

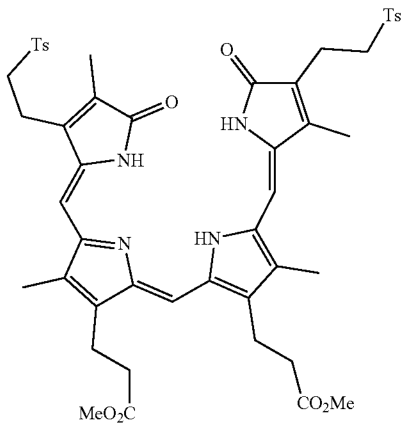

3

1.00 g of 3,7-dimethyl-8-(2-methoxycarbonyl ethyl)-2-(2-neneneba p-toluenesulfonyl ethyl)-dipyrrolomethen-1-one (shown in Formula 14) and 0.87 g of 9-formyl-2,7-dimethyl-8-(2-methoxycarbonyl ethyl)-3-(2-neneneba p-toluenesulfonyl ethyl)-dipyrrolomethen-1-one (shown in Formula 13) were mixed and dissolved in 50 mL of methanol, and then 1.5 mL of 1M hydrogen chloride methanol solution was added. The resulting mixture was stirred at 20° C. for 10 hours, dissolved in 20 mL of dichloromethane. The organic layer was collected, washed with saturated sodium bicarbonate to neutral, dried over anhydrous sodium sulfate, filtered, and recrystallized with ethanol to yield 1.19 g of blue-green solid, that is, 3,3'-(3,18-bis (2-neneneba p-toluenesulfonyl ethyl)-2,7,13,17-tetramethyl-1,19-dioxo-1,19,22,24-tetrahydro-21H-8,12-porphyrin)-dipropionate dimethyl ester (shown in Formula 3), with a yield of 72%.

Example 7

Synthesis of 3,3'-(3-vinyl-18-(2-p-tolylene sulfonyl group ethyl)-2,7,13,17-tetramethyl-1,19-dioxo-1,19,22,24-tetrahydro-21H-8,12-porphyrin)-dipropionate Dimethyl Ester (Shown in Formula 4)

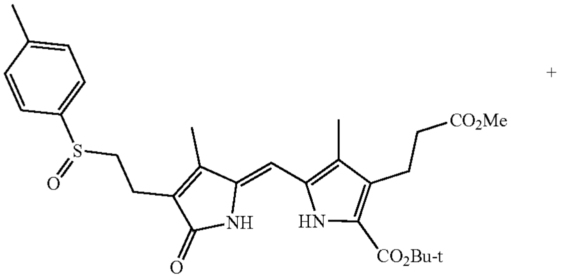

9

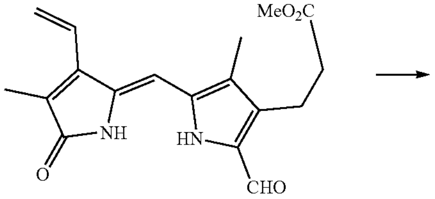

15

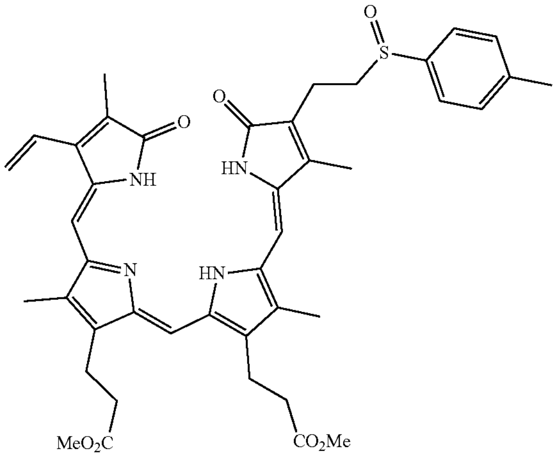

4

1.00 g of 9-tert-butyloxycarbonyl-3,7-dimethyl-8-(2-methoxycarbonyl ethyl)-2-(2-p-tolylene sulfonyl group ethyl)-dipyrrolomethen-1-one (shown in formula 9) was dissolved in 5 mL of trifluoroacetic acid and stirred at room temperature for 30 minutes, and then 0.62 g of 9-formyl-2,7-dimethyl-8-(2-methoxycarbonyl ethyl)-3-vinyl-dipyrrolomethen-1-one (shown in formula 15) was added. the resulting mixture was stirred at 25° C. for 10 hours, extracted with dichloromethane, washed with saturated sodium bicarbonate was to neutral. The organic layer was collected, dried over the anhydrous sodium sulfate, filtered, and recrystallized with ethanol to yield 0.93 g of a blue-green solid, that is, 3,3'-(3-vinyl-18-(2-p-tolylene sulfonyl group ethyl)-2,7,13,17-tetramethyl-1,19-dioxo-1,19,22,24-tetrahydro-21H-8,12-porphyrinyl)-dipropionate dimethyl ester (shown in Formula 4), with a yield of 66%. $^1$H NMR (400 MHz, $CDCl_3$): δ 1.70 (s, 3H), 2.02 (s, 3H), 2.04 (s, 3H), 2.10 (s, 3H), 2.39 (s, 3H), 2.52-2.55 (m, 4H), 2.73-2.78 (m, 2H), 2.86-2.89 (m, 4H), 3.03-3.08 (m, 2H), 3.68 (s, 3H), 5.59 (d, J=17.1, 1H), 5.61 (d, J=10.5, 1H), 5.81 (s, 1H), 5.87 (s, 1H), 6.53 (dd, J=17.1, 11.6 Hz, 1H), 6.65 (s, 1H), 7.29 (d, J=8.2 Hz, 2H), 7.57 (d, J=8.2 Hz, 2H); ESI-Mass: 751.95 $(M+1)^+$.

Example 8

Synthesis of 3,3'-(3-vinyl-18-(2-p-tolylene sulfonyl group ethyl)-2,7,13,17-tetramethyl-1,19-dioxo-1,19,22,24-tetrahydro-21H-8,12-porphyrin)-dipropionate Dimethyl Ester (Shown in Formula 4)

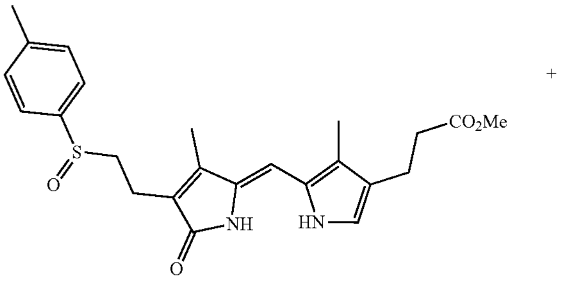

11

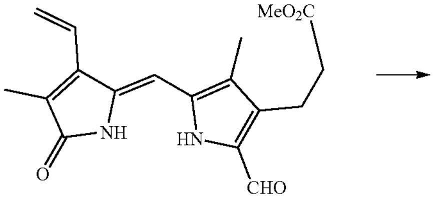

15

-continued

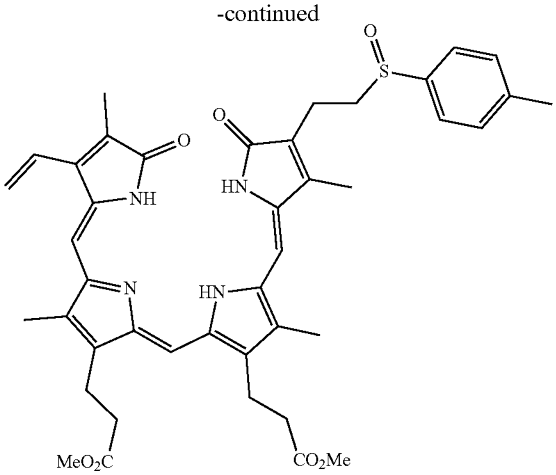

4

1.00 g of 3,7-dimethyl-8-(2-methoxycarbonyl ethyl)-2-(2-neneneba p-toluenesulfonyl ethyl)-dipyrrolidine 1-one (shown in Formula 11) and 0.62 g of 9-formyl-2,7-dimethyl-8-(2-methoxycarbonyl ethyl)-3-vinyl-dipyrrolidine 1-one (shown in Formula 15) were mixed and dissolved with 50 mL of methanol, and then 0.5 mL of concentrated sulfuric acid was added. The resulting mixture was stirred at 25° C. for 10 hours, concentrated under reduced pressure, and dissolved in dichloromethane. The organic layer was collected, washed with the saturated sodium bicarbonate to neutral, dried over anhydrous sodium sulfate, filtered, and recrystallized with ethanol to yield 1.00 g of a blue-green solid, which was 3,3'-(3-vinyl-18-(2-p-tolylene sulfonyl group ethyl)-2,7,13,17-tetramethyl-1,19-dioxo-1,19,22,24-tetrahydro-21H-8,12-porphyrin)-dimethyl dipropionate (shown in Formula 4) in 71% yield.

Example 9

Synthesis of 3,3'-(3-vinyl-18-(2-p-tolylene sulfonyl group ethyl)-2,7,13,17-tetramethyl-1,19-dioxo-1,19,22,24-tetrahydro-21H-8,12-porphyrin)-dipropionate Dimethyl Ester (Shown in Formula 4)

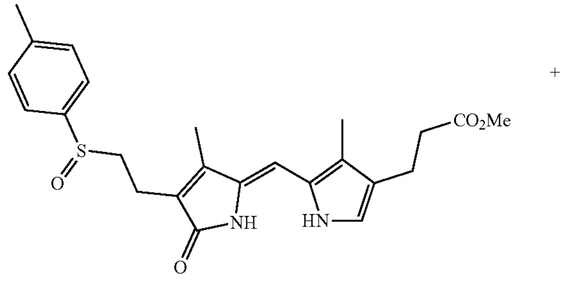

11

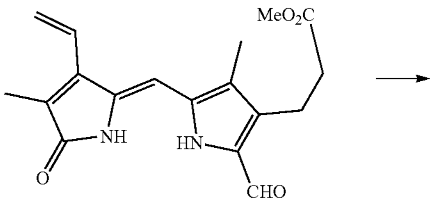

15

-continued

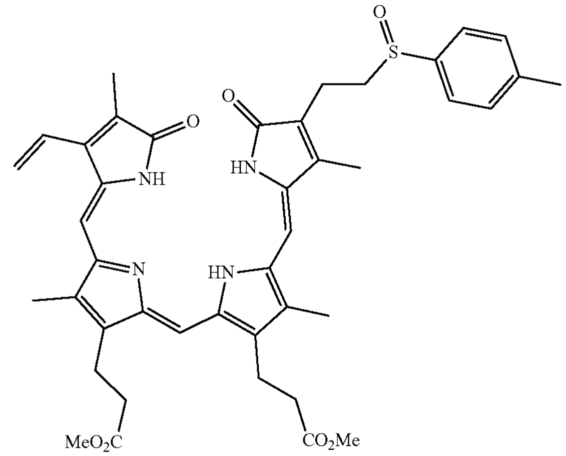

4

1.00 g of 3,7-dimethyl-8-(2-methoxycarbonyl ethyl)-2-(2-neneneba p-toluenesulfonyl ethyl)-dipyrrolidine 1-one (shown in Formula 11) and 0.62 g of 9-formyl-2,7-dimethyl-8-(2-methoxycarbonyl ethyl)-3-vinyl-dipyrrolidine 1-one (shown in Formula 15) were mixed and dissolved with 50 mL of methanol, and then 1.5 mL of 1M hydrogen chloride methanol solution was added. The resulting mixture was stirred at 25° C. for 10 hours, and dissolved in 20 mL of dichloromethane. The organic layer was collected, washed with the saturated sodium bicarbonate to neutral, dried over anhydrous sodium sulfate, filtered, and recrystallized with ethanol to yield 1.19 g of a blue-green solid, which was 3,3'-(3-vinyl-18-(2-p-tolylene sulfonyl group ethyl)-2,7,13,17-tetramethyl-1,19-dioxo-1,19,22,24-tetrahydro-21H-8,12-porphyrin)-dimethyl dipropionate (shown in Formula 4) in 72% yield.

Example 10

Synthesis of Biliverdin Dimethyl Ester

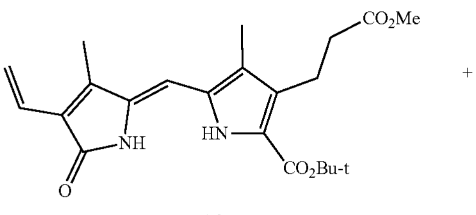

16

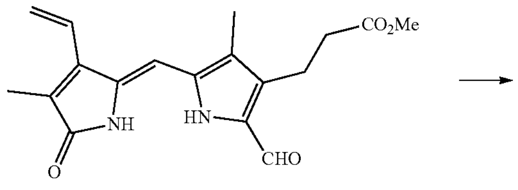

15

-continued

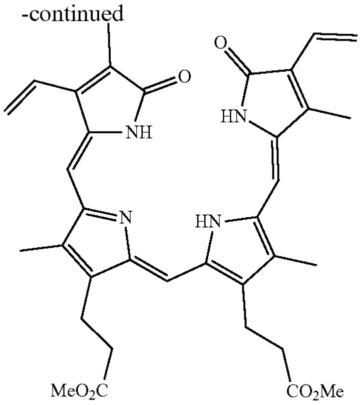

5

1.00 g of 9-tert-butoxycarbonyl-3,7-dimethyl-8-(2-methoxycarbonylethyl)-2-vinyl-dipyrrolidene-1-one (shown in formula 16) was dissolved in 5 mL of trifluoroacetic acid, stirred at room temperature for 30 minutes, and 0.62 g of 9-formyl-2,7-dimethyl-8-(2-methoxycarbonyl-ethyl)-3-vinyl-dipyrrolidene-1-one (c shown in formula 15) was added. The resulting mixture was dissolved in 50 mL of methanol, and then 1.5 mL of 1M hydrogen chloride methanol solution was added, stirred at 25° C. for 10 hours, concentrated under reduced pressure, dissolved in dichloromethane, and washed with saturated sodium bicarbonate to neutral. The organic layer was collected, dried over anhydrous sodium sulfate, filtered, and recrystallized with ethanol to yield 0.93 g of a blue-green solid, that is, biliverdin dimethyl ester, with a yield of 66%. $^1$H NMR (400 MHz, $CDCl_3$): δ 1.89 (s, 3H), 2.10 (s, 3H), 2.13 (s, 3H), 2.20 (s, 3H), 2.56 (t, J=8.1 Hz, 4H), 2.95 (t, J=8.1 Hz, 4H), 3.69 (s, 6H), 5.46 (d, J=12.0 Hz, 1H), 5.66 (dd, J=12.0, 4.0 Hz, 1H), 5.68 (dd, J=16.0, 4.0 Hz, 1H), 6.02 (s, 1H), 6.08 (s, 1H), 6.14 (dd, J=16.0, 4.0 Hz, 1H), 6.51 (dd, J=16.0, 12.0 Hz, 1H), 6.64 (dd, J=16.0, 12.0 Hz, 1H), 6.81 (s, 1H); ESI-Mass: 633.20 $(M+Na)^+$.

Example 11

Synthesis of Biliverdin Dimethyl Ester

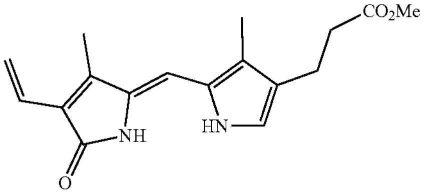

+

17

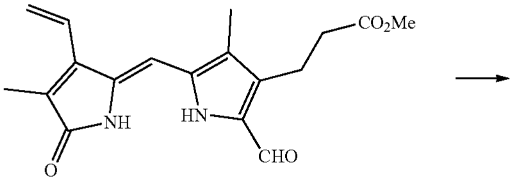

15

-continued

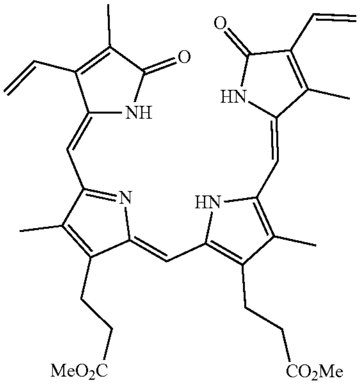

5

1.00 g of 3,7-dimethyl-8-(2-methoxycarbonyl ethyl)-2-vinyl-dipyrrolomethen-1-one (shown in Formula 17) and 0.97 g of 9-formyl-2,7-dimethyl-8-(2-methoxycarbonyl ethyl)-3-p-toluenesulfonyl-dipyrrolomethen-1-one (shown in Formula 15) were mixed and dissolved in 50 mL of methanol, and then 0.5 mL of concentrated sulfuric acid was added. The resulting mixture was stirred at 25° C. for 10 hours, concentrated under reduced pressure, and dissolved in dichloromethane. The organic layer was collected, washed with saturated sodium bicarbonate to neutral, dried over anhydrous sodium sulfate, filtered, and recrystallized with ethyl acetate to yield a blue-green solid, that is, biliverdin dimethyl ester, with a yield of 52%.

Example 12

Synthesis of Biliverdin Dimethyl Ester

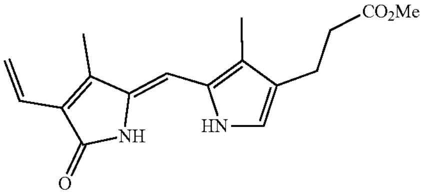

+

17

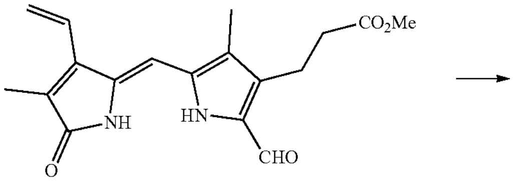

15

-continued

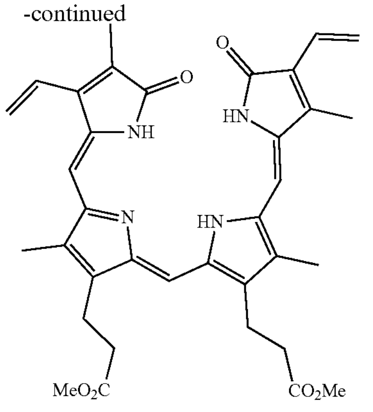

5

1.00 g of 3,7-dimethyl-8-(2-methoxycarbonyl ethyl)-2-vinyl-dipyrrolomethen-1-one (the compound shown in Formula 17) and 0.97 g of 9-formyl-2,7-dimethyl-8-(2-methoxycarbonyl ethyl)-3-p-toluenesulfonyl-dipyrrolomethen-1-one (shown in Formula 15) were mixed and dissolved in 50 mL of methanol, and then 1.5 mL of 1 M hydrogen chloride methanol was added. The resulting mixture was stirred at 25° C. for 10 hours, concentrated under reduced pressure, and dissolved in dichloromethane. The organic layer was collected, washed with saturated sodium bicarbonate to neutral, dried over anhydrous sodium sulfate, filtered, and recrystallized with ethyl acetate to yield a blue-green solid, that is, biliverdin dimethyl ester, with a yield of 57%.

Example 13

Synthesis of Biliverdin from a Precursor of Biliverdin 1) 0.92 g of 3,3'-(3,18-bis (2-p-tolylene sulfonyl group ethyl)-2,7,13,17-tetramethyl-1,19-dioxo-1,19,22,24-tetra-hydro-21H-8,12-porphyrinyl)-dimethyl dipropionate (shown in formula 2) was dissolved in 40 mL of xylene. The mixture was heated to 135° C., stirred for 2 hours, cooled, and evaporated to remove the solvent under reduced pressure. The residue was recrystallized with ethyl acetate to yield a blue-green solid, which was biliverdin dimethyl ester (shown in formula 5), with a yield of 63%. $^{1}H$ NMR (400 MHz, CDCl3): δ 1.89 (s, 3H), 2.10 (s, 3H), 2.13 (s, 3H), 2.20 (s, 3H), 2.56 (t, J=8.1 Hz, 4H), 2.95 (t, J=8.1 Hz, 4H), 3.69 (s, 6H), 5.46 (d, J=12.0 Hz, 1H), 5.66 (dd, J=12.0, 4.0 Hz, 1H), 5.68 (dd, J=16.0, 4.0 Hz, 1H), 6.02 (s, 1H), 6.08 (s, 1H), 6.14 (dd, J=16.0, 4.0 Hz, 1H), 6.51 (dd, J=16.0, 12.0 Hz, 1H), 6.64 (dd, J=16.0, 12.0 Hz, 1H), 6.81 (s, 1H); ESI-Mass: 633.20 $(M+Na)^{+}$.

The reaction formula is as follows:

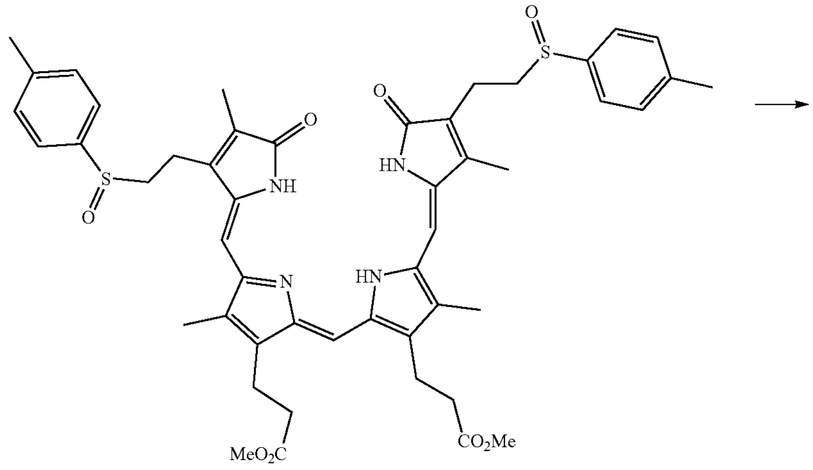

3

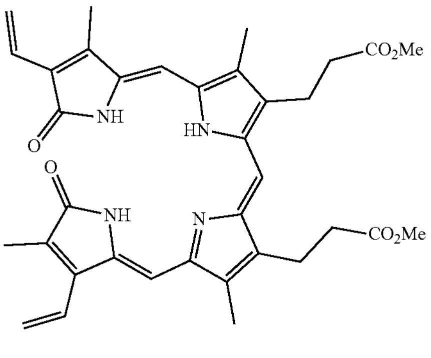

5

2) 0.92 g of 3,3'-(3,18-bis (2-p-toluenesulfonyl ethyl)-2,7,13,17-tetramethyl-1,19-dioxo-1,19,22,24-tetrahydro-21H-8,12-porphyrinyl)-dimethyl dipropionate (shown in Formula 3) was dissolved in 40 mL of anhydrous THF, and then 0.93 g of tert butanol sodium dissolved in 10 mL of tert butanol was added. The resulting mixture was heated to 135° C., stirred for 2 hours, cooled down, and evaporated to remove the solvent under reduced pressure. The residue was mixed with water, acidified with dilute hydrochloric acid, and extracted with dichloromethane, to yield 0.50 g of blue-green solid, which was biliverdin (shown in Formula 6), with a yield of 74%. The spectral data of the product is in reference to the literature Monatshr Chem., 1989, 120, 575-580.

The reaction formula is as follows:

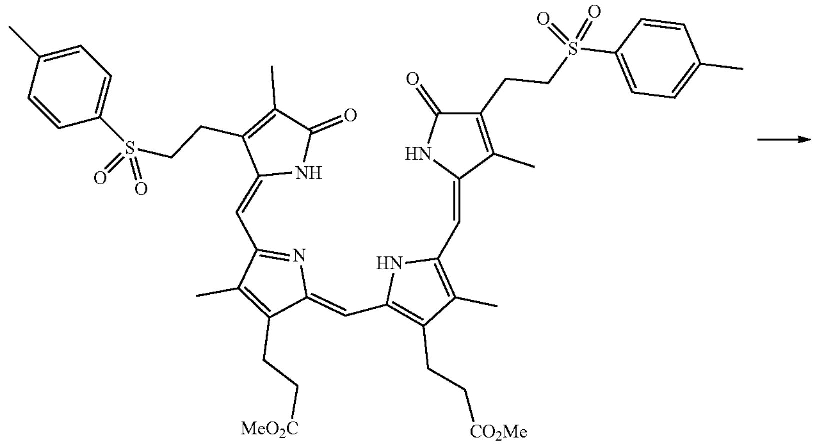

3

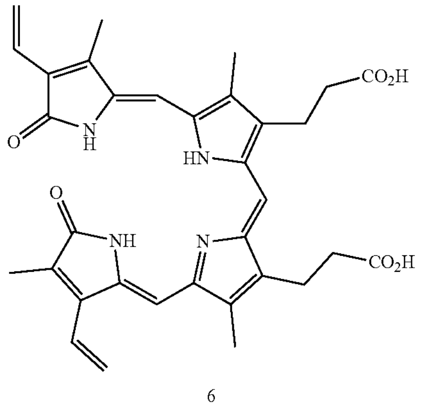

6

3) 0.92 g of 3,3'-(3-vinyl-18-(2-p-tolylene sulfonyl group ethyl)-2,7,13,17-tetramethyl-1,19-dioxo-1,19,22,24-tetrahydro-21H-8,12-porphyrinyl)-dimethyl dipropionate (shown in Formula 4) was dissolved in 40 mL of DMF and heated to 130° C. The mixture was stirred for 2 hours, cooled, evaporated to remove the solvent under reduced pressure, and the residue was recrystallized with ethyl acetate to yield a blue-green solid, which was biliverdin dimethyl ester shown in Formula 5), with a yield of 60%.

The reaction formula is as follows:

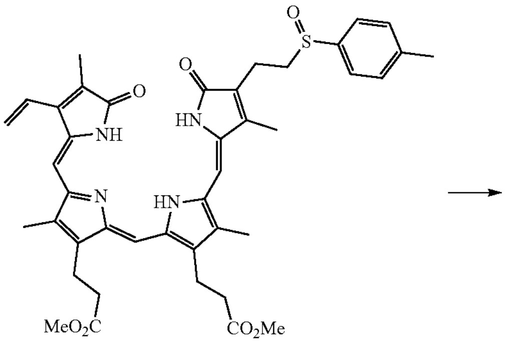

4

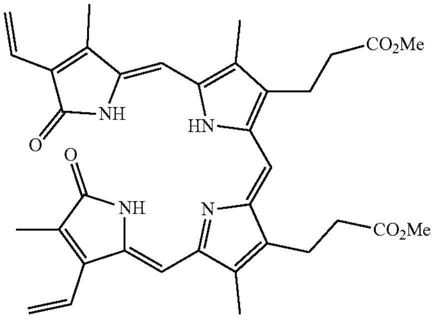

5

Example 14

1. Synthesis of 9-tert-butyloxycarbonyl-3,7-dimethyl-8-(2-methoxycarbonyl ethyl)-2-(2-p-tolylene sulfonyl group ethyl)-dipyrrolomethen-1-one (shown in Formula 9)

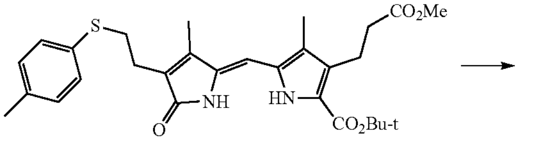

18

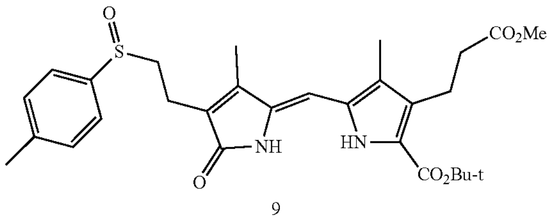

9

5.24 g of the compound shown in Formula 18 was put into a reaction flask, dissolved in 30 mL of dichloromethane. The mixture was cooled to 0° C., and 2.40 g of 85% m-chloro perbenzoic acid was added in batches. The mixture was stirred at room temperature for 3 hours, washed with saturated sodium bisulfate solution. The organic layer was collected, and then washed successively with saturated salt water and water, dried over anhydrous sodium sulfate, filtered, concentrated to yield 4.97 g of a yellow solid, that is, 9-tert-butyloxycarbonyl-3,7-dimethyl-8-(2-methoxycarbonyl ethyl)-2-(2-p-tolylene sulfonyl group ethyl)-dipyrrolomethen-1-one (shown in Formula 9), with a yield of 92%. The final product was directly used for the next reaction. $^1$H NMR (400 MHz, $CDCl_3$): δ 1.57 (s, 9H), 2.08 (s, 3H), 2.15 (s, 3H), 2.30 (s, 3H), 2.54 (t, J=8.0 Hz, 2H), 2.80 (t, J=7.2 Hz, 2H), 3.03 (t, J=8.0 Hz, 2H), 3.17 (t, J=7.2 Hz, 2H), 3.70 (s, 3H), 6.00 (s, 1H), 7.03 (d, J=8.0 Hz, 2H), 7.23 (d, J=8.0 Hz, 2H), 9.89 (s, 1H), 10.20 (s, 1H); ESI-Mass: 563.25 $(M+Na)^+$.

2. Synthesis of 9-tert butoxycarbonyl-3,7-dimethyl-8-(2-methoxycarbonylethyl)-2-(2-p-toluenesulfoethyl)-dipyrrolidene-1-one (shown in formula 18)

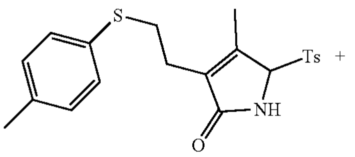

19

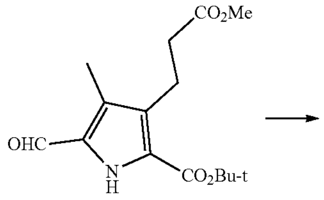

20

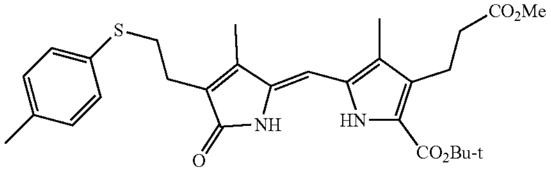

18

Under nitrogen protection, 10.50 g of the compound shown in formula 19 and 14.85 g of the compound shown in formula 20 were mixed and dissolved in 250 mL of anhydrous THF. Thereafter, 16.55 g of tri-n-butylphosphorus and 6.50 g of DBU were sequentially added and stirred at room temperature for 12 hours, and 1.0 g of solid iodine was further added. The mixture was further stirred at room temperature for 12 hours, concentrated under reduced pressure, and 20 mL of ethanol was added. A solid was precipitated, filtered, and washed with ethanol to yield 13.60 g of a yellow solid, that is, 9-tert butyloxycarbonyl-3,7-dimethyl-8-(2-methoxycarbonylethyl)-2-(2-p-toluenesulfoethyl)-dipyrrolidene-1-one (shown in formula 18), with a yield of 73%. $^1$H NMR (400 MHz, $CDCl_3$): δ 1.56 (s, 9H), 2.07 (s, 3H), 2.13 (s, 3H), 2.28 (s, 3H), 2.54 (t, J=8.1 Hz, 2H), 2.80 (t, J=7.1 Hz, 2H), 3.03 (t, J=8.1 Hz, 2H), 3.15 (t, J=7.1 Hz, 2H), 3.70 (s, 3H), 6.00 (s, 1H), 7.03 (d, J=8.0 Hz, 2H), 7.23 (d, J=8.0 Hz, 2H), 9.89 (s, 1H), 10.18 (s, 1H), 10.71 (s, 1H); ESI-Mass: 446.20 $(M+Na)^+$.

3. Synthesis of 9-formyl-3,7-dimethyl-8-(2-methoxycarbonyl ethyl)-2-(2-p-tolylene sulfonyl group ethyl)-dipyrrolomethen-1-one (Shown in Formula 10)

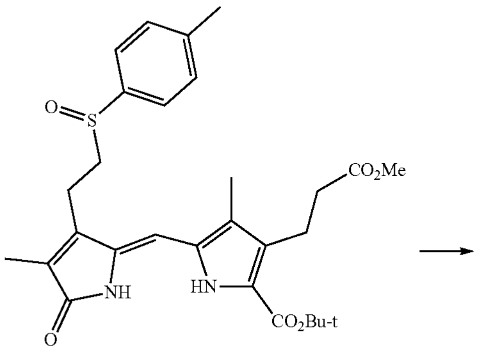

21

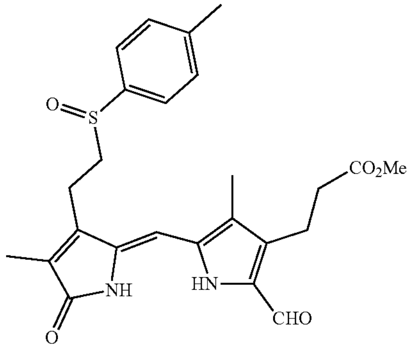

10

5.00 g (9.3 mmol) of 9-tert-butyloxycarbonyl-2,7-dimethyl-8-(2-methoxycarbonyl ethyl)-3-(2-p-tolylene sulfonyl group ethyl)-dipyrrolomethen-1-one (shown in Formula 21) was dissolved in 20 mL of trifluoroacetic acid, stirred at room temperature for 30 minutes, and then 20 mL of trimethyl orthoformate was added. The mixture was further stirred at room temperature for 1 hour, mixed with water, extracted with dichloromethane, washed with saturated sodium bicarbonate to neutral, washed with water, dried with anhydrous sodium sulfate, filtered, concentrated and recrystallized with ethanol to yield 2.24 g of a yellow solid, namely 9-formyl-3,7-dimethyl-8-(2-methoxycarbonyl ethyl)-2-(2-p-tolylene sulfonyl group ethyl)-dipyrrolomethen-1-one (shown in Formula 10), with a yield of 55%. $^1$H NMR (400 MHz, $CDCl_3$): δ 1.93 (s, 3H), 2.07 (s, 3H), 2.43 (s, 3H), 2.56 (t, J=7.6 Hz, 2H), 2.66-2.70 (m, 1H), 2.88-2.92 (m, 1H), 2.95-3.10 (m, 4H), 3.65 (s, 3H), 5.98 (s, 1H), 7.34 (d, J=8.0 Hz, 2H), 7.51 (d, J=8.0 Hz, 2H), 9.72 (s, 1H), 10.78 (s, 1H), 10.91 (s, 1H); ESI-Mass: 491.22 $(M+Na)^+$.

4. Synthesis of 3,7,9-trimethyl-8-(2-methoxycarbonyl ethyl)-2-(2-p-tolylene sulfonyl group ethyl)-dipyrrolomethen-1-one (Shown in Formula 11)

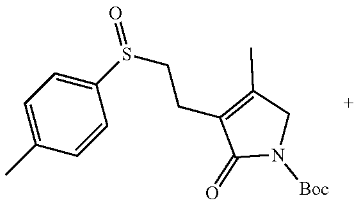

22

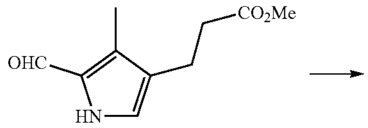

23

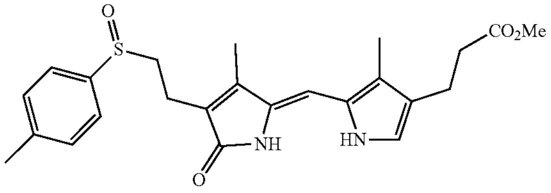

11

3.63 g of 1-tert-butyloxycarbonyl-3-p-tolylene sulfonyl group ethyl-4-methyl-1,5-dihydro-2H-2-pyrrolidone (shown in Formula 22) and 1.95 g of 4-methoxycarbonyl-ethyl-3-methyl-2-pyrrolialdehyde (shown in Formula 23) were dissolved in 20 mL of toluene, and then 4.0 mL of DBU was added, stirred at 90° C. for 10 hours, cooled down, evaporated to remove the solvent under reduced pressure. The residue was dissolved in dichloromethane, acidified with dilute hydrochloric acid to pH 5. The dichloromethane layer was collected, concentrated, and the residue was recrystallized with ethanol to yield 2.24 g of a yellow solid, which was 3,7,9-trimethyl-8-(2-methoxycarbonyl ethyl)-2-(2-p-tolylene sulfonyl group ethyl)-dipyrrolomethen-1-one (shown in Formula 11) in 51% yield. 1H NMR (400 MHz, CDCl3): δ 1.26 (t, J=7.2 Hz, 3H), 2.11 (s, 3H), 2.16 (s, 3H), 2.28 (s, 3H), 2.57 (t, J=8.0 Hz, 2H), 2.70-2.77 (m, 4H), 3.14 (t, J=7.2 Hz, 2H), 4.16 (q, J=7.2 Hz, 2H), 6.22 (s, 1H), 6.79 (d, J=2.4 Hz, 2H), 7.07 (d, J=8.0 Hz, 2H), 7.25 (d, J=8.0 Hz, 2H), 10.51 (s, 1H), 11.15 (s, 1H); ESI-Mass: 477.22 $(M+Na)^+$.

5. Synthesis of N-tert butoxycarbonyl-3-(2-p-toluenesulfonyl ethyl)-4-methyl-1H-2 (5H) pyrrolidone (shown in formula 22)

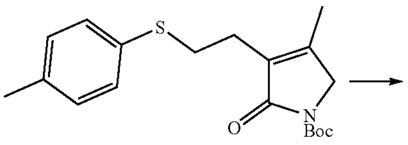

24

-continued

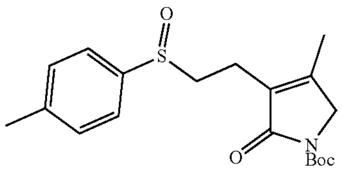

22

3.47 g of the compound shown in Formula 24 was dissolved in 50 mL of dichloromethane, cooled to 0° C., and 2.21 g of 85% m-chloro perbenzoic acid was added in batches. The mixture was stirred for 2 hours at below 5° C., washed with 10% sodium bisulfite solution. The organic layer was collected, washed with saturated salt water, dried with anhydrous sodium sulfate, filtered, concentrated to yield 3.48 g of a light yellow oily product, which was N-tert butyloxycarbonyl-3-(2-p-toluenesulfonyl ethyl)-4-methyl-1H-2 (5H) pyrrolidone (shown in formula 22) in a yield of 95% and can be directly used for next reaction.

6. Synthesis of N-tert butoxycarbonyl-3-(2-p-tolyl-thioethyl)-4-methyl-1H-2 (5H) pyrrolidone (shown in formula 24)

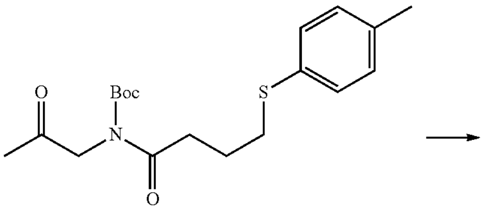

25

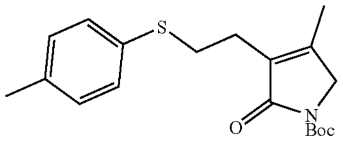

24

6.80 g of the compound shown in formula 25 was mixed with 50 mL of DMSO comprising 3.0 g of sodium hydroxide, stirred at room temperature for 30 minutes. The mixture was poured into 100 mL of ice water, extracted with ethyl acetate, washed with dilute hydrochloric acid to neutral, washed with saturated salt water, dried over anhydrous sodium sulfate, filtered, concentrated, and recrystallized with ethanol to yield 6.0 g of earthy yellow solid, that is, N-tert butoxycarbonyl-3-(2-p-tolylthioethyl)-4-methyl-1H-2 (5H) pyrrolidone shown in formula 24), with a yield of 84%. $^{1}$H NMR (400 MHz, $CDCl_3$): $\delta$1.55 (s, 9H), 61.95 (s, 3H), 2.30 (s, 3H), 2.57 (t, J=7.2 Hz, 2H), 3.11 (t, J=7.2 Hz, 2H), 4.03 (s, 2H), 7.08 (d, J=8.0 Hz, 2H), 7.25 (d, J=8.0 Hz, 2H); ESI-Mass: 717.14 (2M+Na)$^+$.

7. Synthesis of N-acetonyl-N-tert-butyloxycarbonyl-4-p-toluenesulfobutylamide (shown in formula 25)

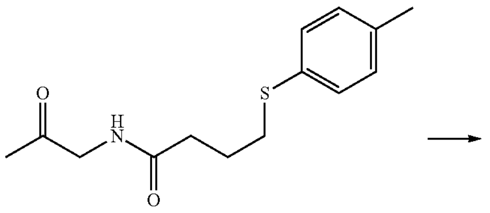

26

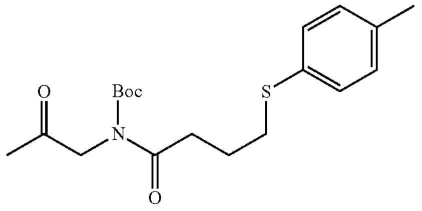

25

8 g of the compound shown in formula 26 was dissolved in 50 mL of dichloromethane, and then 8.0 g of DMAP was added, cooled to 0° C. 13.2 g of Boc2O dissolved in 90 mL of dichloromethane was added, and the temperature was controlled to not exceed 5° C. The mixture was stirred at 15-30° C. for 10 hours, poured into 100 mL of ice water, and acidified with dilute hydrochloric acid to pH 3. The organic layer was collected, washed with saturated sodium bicarbonate and salt water, dried with anhydrous sodium sulfate, filtered, and concentrated, to yield 10.81 g of a light yellow liquid, which was N-acetonyl-N-tert-butyloxycarbonyl-4-p-toluenesulfobutylamide (shown in formula 25), with a yield of 99%. $^{1}$H NMR (400 MHz, $CDCl_3$): $\delta$1.47 (s, 9H), 1.93-1.97 (m, 2H), 2.14 (s, 3H), 2.30 (s, 3H), 2.93 (t, J=6.0 Hz, 2H), 3.08 (t, J=7.2 Hz, 2H), 4.49 (s, 2H), 7.08 (d, J=8.2 Hz, 2H), 7.25 (d, J=8.2 Hz, 2H); ESI-Mass: 387.97 (M+Na)$^+$.

8. Synthesis of N-Acetone-4-p-Toluenesulfobutylamide (shown in formula 26)

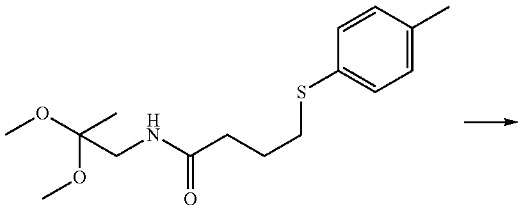

27

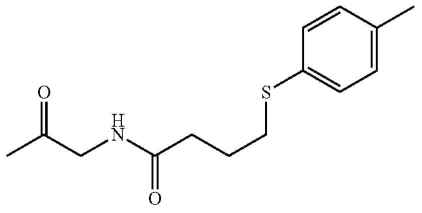

26

11.73 g of the compound shown in formula 27 was dissolved in 50 mL of dichloromethane, and 8.0 g (10.8 mmol) of 5% dilute hydrochloric acid was added. The mixture was stirred at room temperature for 4 hours, allowed to stand, and the dichloromethane layer was collected, washed respectively with saturated salt water and water, dried with anhydrous sodium sulfate, filtered, and concentrated to yield 10.20 g of a white solid, namely, N-acetone-4-p-toluenesulfobutanamide (shown in formula 26), with a yield of 96%. $^1$H NMR (400 MHz, $CDCl_3$): δ1.92-1.97 (m, 2H), 2.20 (s, 3H), 2.31 (s, 3H), 2.39 (t, 6.8 Hz, 2H), 2.93 (t, J=6.8 Hz, 2H), 4.14 (d, J=4.0 Hz, 2H), 6.22 (s, 1H), 7.09 (d, J=4.0 Hz, 2H), 7.26 (d, J=8.0 Hz, 2H); ESI-Mass: 266.0 $(M+H)^+$.

9. Synthesis of N-(2,2-dimethoxypropyl)-4-p-toluenesulfobutanamide (shown in formula 27)

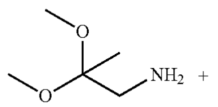

28

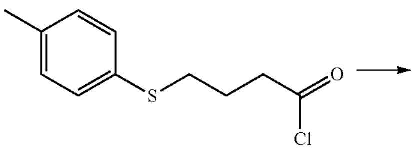

29

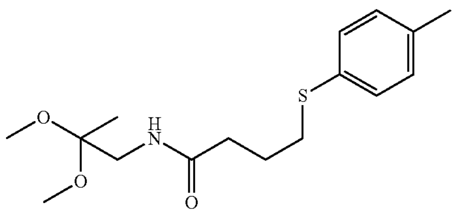

27

6.80 g of 2,2-dimethoxypropylamine (shown in formula 28, 57.1 mmol) was dissolved in 20 mL of dichloromethane. Then 6.10 g of triethylamine (60.4 mmol) was added. The mixture was cooled to 0° C., and 13.03 g (57.1 mmol) of 4-p-toluenesulfobutyryl chloride (shown in formula 29) dissolved in 20 mL of dichloromethane was slowly added dropwise. The temperature was controlled below 5° C. The mixture was stirred at 20-30° C. for 10 hours, filtered, to yield N-(2,2-dimethoxypropyl)-4-p-toluenesulfobutylamide (shown in formula 27). The filter cake was washed with dichloromethane, and the filtrate was directly used for next reaction.

10. Synthesis of 9-formyl-3,7-dimethyl-8-(2-methoxycarbonyl ethyl)-2-(2-p-tolylene sulfonyl group ethyl)-dipyrrolomethen-1-one (Shown in Formula 13)

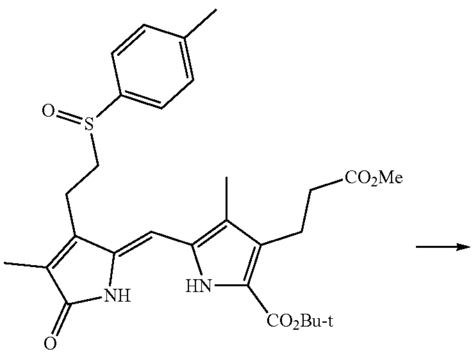

30

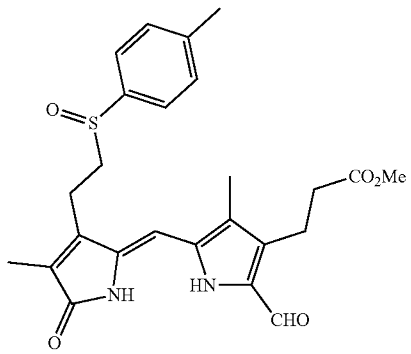

13

5.00 g (9.3 mmol) of 9-tert-butyloxycarbonyl-2,7-dimethyl-8-(2-methoxycarbonyl ethyl)-3-(2-p-tolylene sulfonyl group ethyl)-dipyrrolomethen-1-one (shown in Formula 30) was dissolved in 20 mL of trifluoroacetic acid, stirred at room temperature for 30 minutes, and then 20 mL of trimethyl orthoformate was added. The mixture was stirred at room temperature for 1 hour, mixed with water, extracted with dichloromethane, washed with saturated sodium bicarbonate to neutral, washed with water, dried over anhydrous sodium sulfate, filtered, concentrated and recrystallized with ethanol to yield 2.24 g of a yellow solid, namely 9-formyl-3,7-dimethyl-8-(2-methoxycarbonyl ethyl)-2-(2-p-tolylene sulfonyl group ethyl)-dipyrrolomethen-1-one (shown in Formula 13) in 55% yield. $^1$H NMR (400 MHz, $CDCl_3$): δ 1.93 (s, 3H), 2.07 (s, 3H), 2.43 (s, 3H), 2.56 (t, J=7.6 Hz, 2H), 2.66-2.70 (m, 1H), 2.88-2.92 (m, 1H), 2.95-3.10 (m, 4H), 3.65 (s, 3H), 5.98 (s, 1H), 7.34 (d, J=8.0 Hz, 2H), 7.51 (d, J=8.0 Hz, 2H), 9.72 (s, 1H), 10.78 (s, 1H), 10.91 (s, 1H); ESI-Mass: 491.22 $(M+Na)^+$.

11. Synthesis of 3,7,9-trimethyl-8-(2-methoxycarbonyl ethyl)-2-(2-neneneba p-toluenesulfonyl ethyl)-dipyrrolomethen-1-one (Formula 14)

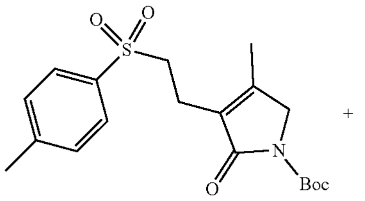

31

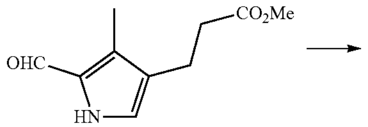

23

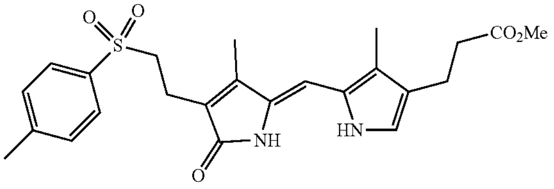

14

3.67 g of 1-tert-butyloxycarbonyl-3-p-tolylene sulfonyl group ethyl-4-methyl-1,5-dihydro-2H-2-pyrrolidone (shown in Formula 31) and 1.95 g of 4-methoxycarbonyl-ethyl-3-methyl-2-pyrrolialdehyde (shown in Formula 23) were dissolved in 20 mL of toluene, and then 4.0 mL of DBU was added. The mixture was stirred at 90° C. for 10 hours, cooled down, evaporated to remove the solvent under reduced pressure. The residue was dissolved in dichloromethane, acidified with dilute hydrochloric acid to pH 5. The dichloromethane layer was collected, concentrated, and the residue was recrystallized with ethanol to yield 2.24 g of a yellow solid, which was 3,7,9-trimethyl-8-(2-methoxycarbonyl ethyl)-2-(2-neneneba p-toluenesulfonyl ethyl)-dipyrrolomethen-1-one (shown in Formula 14), with a yield of 51%. $^1H$ NMR (400 MHz, $CDCl_3$): δ1.26 (t, J=7.2 Hz, 3H), 2.11 (s, 3H), 2.16 (s, 3H), 2.28 (s, 3H), 2.57 (t, J=8.0 Hz, 2H), 2.70-2.77 (m, 4H), 3.14 (t, J=7.2 Hz, 2H), 4.16 (q, J=7.2 Hz, 2H), 6.22 (s, 1H), 6.79 (d, J=2.4 Hz, 2H), 7.07 (d, J=8.0 Hz, 2H), 7.25 (d, J=8.0 Hz, 2H), 10.51 (s, 1H), 11.15 (s, 1H); ESI-Mass: 477.22 $(M+Na)^+$.

12. Synthesis of N-tert butoxycarbonyl-3-(2-p-toluenesulfonyl ethyl)-4-methyl-1H-2 (5H) pyrrolidone (shown in formula 31)

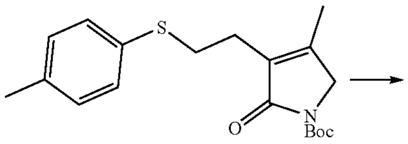

-continued

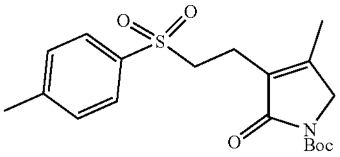

3.47 g of the compound shown in formula 24 was dissolved in 50 mL of methanol, and then 5.7 mL of 30% hydrogen peroxide was added. The mixture was kept at 75° C. for 2 hours, washed with a 10% sodium bisulfite solution, and extracted with dichloromethane. The organic layer was collected, washed with saturated salt water, dried with anhydrous sodium sulfate, filtered, and concentrated to yield 3.47 g of a light yellow oily product, which was N-tert butoxycarbonyl-3-(2-p-toluenesulfonyl ethyl)-4-methyl-1H-2 (5H) pyrrolidone (shown in formula 31), with a yield of 91%, directly used for next reaction.

It will be obvious to those skilled in the art that changes and modifications may be made, and therefore, the aim in the appended claims is to cover all such changes and modifications.

What is claimed is:

1. An intermediate of biliverdin represented by formula 1:

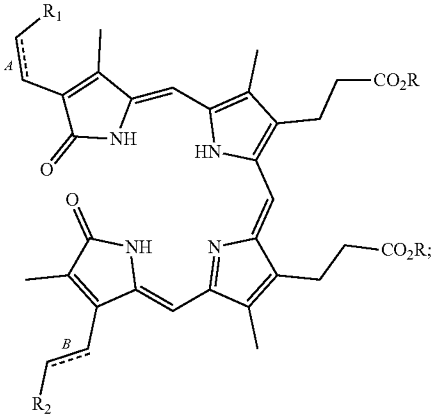

wherein:

R is $C_1$-$C_5$ alkyl, or benzyl; "---" at positions A and B independently represent a single bond or a double bond;

when "---" represents a single bond, $R_1$ or $R_2$ connected to the single bond is selected from p-toluenesulfonyl, p-toluenesulfinyl, phenylsulfonyl, and phenylsulfinyl; and when "---" represents a double bond, $R_1$ or $R_2$ connected to the double bond is hydrogen, and wherein at least one of $R_1$ or $R_2$ is selected from p-toluenesulfonyl, p-toluenesulfinyl, phenylsulfonyl, and phenylsulfinyl.

2. The intermediate of biliverdin of claim 1, wherein the intermediate of biliverdin represented by formula 1 is one of the following compounds:

2

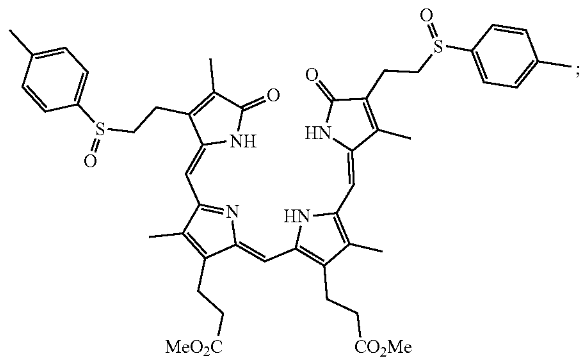

;

3

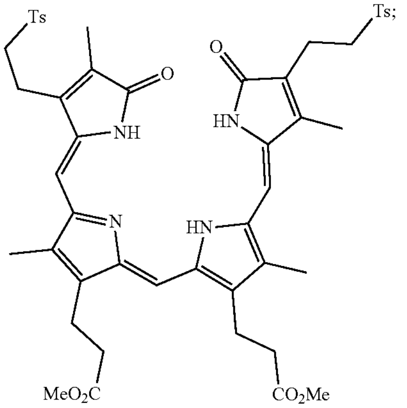

3. A method for preparing the intermediate of biliverdin of claim 1, the method comprising contacting a compound represented by formula 7 and a compound represented by formula 8 for a condensation reaction:

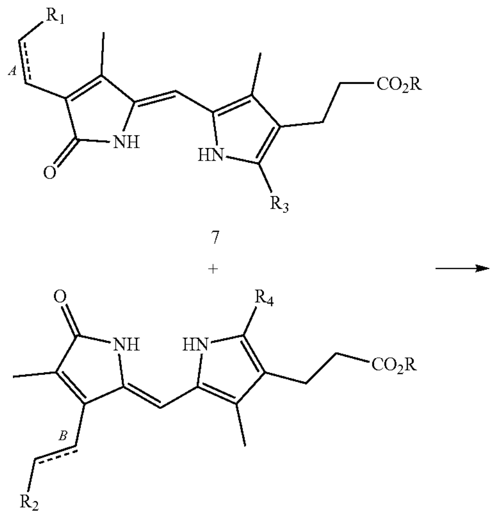

7

+

8

-continued

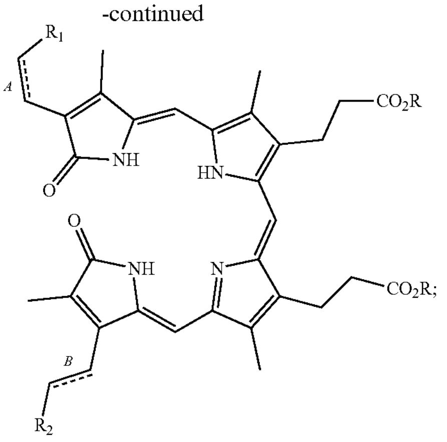

1

R is $C_1$-$C_5$ alkyl, or benzyl; "---" at positions A and B independently represent a single bond or a double bond;

when "---" represents a single bond, $R_1$ or $R_2$ connected to the single bond is selected from p-toluenesulfonyl, p-toluenesulfinyl, phenylsulfonyl, phenylsulfinyl; when "---" represents a double bond, $R_1$ or $R_2$ connected to the double bond is hydrogen; and one of $R_3$ and $R_4$ is a formyl, and the other is tert-butoxycarbonyl or hydrogen, and wherein at least one of $R_1$ or $R_2$ is selected from p-toluenesulfonyl, p-toluenesulfinyl, phenylsulfonyl, and phenylsulfinyl.

4. The method of claim 3, wherein the condensation reaction is carried out in the presence of an acid as a catalyst.

5. The method of claim 4, wherein the acid is hydrochloric acid, sulfuric acid, trifluoroacetic acid, formic acid, acetic acid, benzenesulfonic acid, p-toluenesulfonic acid, or a mixture thereof.

6. The method of claim 3, wherein the condensation reaction is conducted in a solvent selected from $C_1$-$C_6$ alcohol, dichloromethane, tetrahydrofuran, 1,2-dichloroethane, ethyl acetate, acetone, or a mixture thereof.

7. The method of claim 3, wherein the condensation reaction is carried out at a temperature of between −10° C. and 35° C.

8. The method of claim 4, wherein a molar ratio of the compound 7 to the compound 8 to the acid is 1:(0.5-2):(0.1-0.5).

* * * * *